US006416737B1

(12) United States Patent
Manolagas et al.

(10) Patent No.: US 6,416,737 B1
(45) Date of Patent: Jul. 9, 2002

(54) INCREASING BONE STRENGTH WITH SELECTED BISPHOSPHONATES

(75) Inventors: Stavros C. Manolagas; Teresita Bellido, both of Little Rock, AR (US)

(73) Assignee: Board of Trustees of the University of Arkansas, Little Rock, AK (US)

( * ) Notice: Subject to any disclaimer, the term of this patent is extended or adjusted under 35 U.S.C. 154(b) by 0 days.

(21) Appl. No.: 09/443,841

(22) Filed: Nov. 19, 1999

Related U.S. Application Data

(60) Provisional application No. 60/109,237, filed on Nov. 19, 1998, and provisional application No. 60/165,480, filed on Nov. 15, 1999.

(51) Int. Cl.$^7$ .......................... A61K 49/00; A61K 31/66; G01N 33/15
(52) U.S. Cl. .......................... 424/9.2; 424/9.6; 436/103; 436/104; 436/106; 436/111; 436/127; 514/75; 514/102; 514/114; 514/141
(58) Field of Search .......................... 424/9.1, 9.2, 9.6; 436/103, 104, 106, 111, 127; 514/75, 102, 114, 139, 141

(56) References Cited

U.S. PATENT DOCUMENTS

| | | | |
|---|---|---|---|
| 4,522,811 A | 6/1985 | Eppstein et al. ............ 424/85.1 |
| 4,588,716 A | 5/1986 | DeLuca et al. ............. 514/168 |
| 4,619,920 A | 10/1986 | DeLuca et al. ............. 514/167 |
| 4,710,382 A | 12/1987 | Recker ........................ 514/12 |
| 4,833,125 A | 5/1989 | Neer et al. ................... 514/12 |
| 4,870,054 A | 9/1989 | Recker ........................ 514/12 |
| 4,870,063 A | 9/1989 | Binderup et al. ............. 514/79 |
| 4,970,237 A | 11/1990 | Jensen et al. ............... 514/651 |
| 4,973,584 A | 11/1990 | DeLuca et al. ............. 514/167 |
| 5,001,118 A | 3/1991 | Maeda et al. ............... 514/167 |
| 5,071,655 A | 12/1991 | Baylink ....................... 424/422 |
| 5,104,864 A | 4/1992 | DeLuca ........................ 514/167 |
| 5,118,667 A | 6/1992 | Adams et al. ............... 514/12 |
| 5,164,368 A | 11/1992 | Recker ........................ 514/12 |
| 5,183,815 A | 2/1993 | Saari et al. ................... 514/172 |
| 5,208,219 A | 5/1993 | Ogawa et al. ................ 514/12 |
| 5,260,290 A | 11/1993 | DeLuca et al. ............. 514/167 |
| 5,300,687 A | 4/1994 | Schwender et al. ............ 564/15 |
| 5,354,773 A | 10/1994 | Herslof et al. ............... 514/450 |
| 5,403,831 A | 4/1995 | DeLuca et al. ............. 514/167 |
| 5,414,098 A | 5/1995 | DeLuca et al. ............. 552/653 |
| 5,510,370 A | 4/1996 | Hock ........................... 514/443 |
| 5,532,226 A | 7/1996 | Demarest et al. ............ 514/134 |
| 5,532,391 A | 7/1996 | DeLuca et al. ............. 552/653 |
| 5,565,444 A | 10/1996 | Mizushima et al. ........ 514/178 |
| 5,593,833 A | 1/1997 | Morrison et al. ............... 435/6 |
| 5,593,988 A | 1/1997 | Tahara et al. ................ 514/219 |
| 5,604,259 A | 2/1997 | Jee ............................. 514/570 |
| 5,618,549 A | 4/1997 | Patel et al. ................... 424/422 |
| 5,663,195 A | 9/1997 | Scolnick ....................... 514/461 |
| 5,674,844 A | 10/1997 | Kuberasampath et al. .... 514/12 |
| 5,750,746 A | 5/1998 | DeLuca et al. ............. 552/653 |
| 5,753,649 A | 5/1998 | Tahara et al. ................ 514/220 |
| 5,824,672 A | 10/1998 | Simpkins et al. ............ 514/182 |
| 5,843,934 A | 12/1998 | Simpkins ..................... 514/182 |
| 5,859,001 A | 1/1999 | Simpkins et al. ............ 514/185 |
| 5,885,973 A | 3/1999 | Papapoulos et al. .......... 51/106 |
| 6,015,801 A | 1/2000 | Diafotis et al. ............. 514/108 |
| 6,080,779 A | * | 6/2000 | Gasper et al. ............... 514/451 |

FOREIGN PATENT DOCUMENTS

| | | | |
|---|---|---|---|
| EP | 0 753 423 | * | 1/1997 |
| WO | WO 95/26719 | | 10/1995 |
| WO | WO 97/02827 | | 1/1997 |
| WO | WO 98/22113 | | 5/1998 |
| WO | WO 98/31381 | | 7/1998 |

OTHER PUBLICATIONS

STN/CAS online, file EMBASE, Acc. No. 97381244, Doc. No. 1997381244, (Kato et al., 'Establishment of an osteocyte–like cell line, MLO–Y4', Journal of Bone and Mineral Research (1997), 12/12, pp. 2014–23).*

Hill et al., "Multiple Extracellular Signals Promote Osteoblast Survival and Apoptosis" *Endocrinology*, (1997), vol. 138, pp. 3849–3858.

Aarden, E.M., et al., Function of Osteocytes in Bone, J. Cell. Biochem. 55:287–299 (1994).

Alessi, D.R., et al. PD 098059 Is a Specific Inhibitor of the Activation of Mitogen–activated Protein Kinase in Vitro and In Vivo, J. Biol. Chem. 270:27489–27494 (1995).

Ashkenaze, A. and Vishiva M. Dixit. Death Receptors: Signaling and Modulation, Science 281:1305–1308 (1998).

Azria, Moise and Louis V. Avioli. Calcitionin In: Principles of Bone Biology. 1083–1097 (1996) J.P. Bilezikian, L.G. Raisz, and G.A. Rodan eds. Academic Press San Diego, USA.

Balena, R. et al. The Effects of 2–year Treatment with the Aminobisphosphonate Alendronate on Bone Metabolism, Bone Histomorphometry, and Bone Strength in Ovariectomized Nonhuman Primates, J. Clin. Invest. 92:1597–3098 (1993).

Bellido, T. et al. Overexpression of Bcl–2 Renders Osteoblastic Cells Refractory to Glucocorticoid–Induced Apoptosis, Bone, 23:S324, 1998.

(List continued on next page.)

*Primary Examiner*—Jose G. Dees
*Assistant Examiner*—Frank Choi
(74) *Attorney, Agent, or Firm*—King & Spalding; Sherry M. Knowles; Joseph M. Bennett-Paris

(57) ABSTRACT

The present invention is a method and composition to increase bone strength in a manner that decreases fracture incidence, which may or may not include increasing bone mineral density ("BMD"). The invention includes administering an effective amount of a bisphosphonate to a host in need thereof to increase bone strength, which inhibits the apoptosis of osteoblasts and osteocytes, without a significant effect on osteoclasts. In one embodiment, the bisphosphonate is not 1-amino-3-(N,N-dimethylamino)-propyliden-1, 1-bisphosphonic acid or its pharmaceutically acceptable salt. An increase in osteoblast life span can lead to an increase in bone mass, i.e., an anabolic effect. Preservation of osteocyte life span can increase bone strength, which may be disproportional to the increase in bone mass.

7 Claims, 9 Drawing Sheets

OTHER PUBLICATIONS

Bellido, T. et al. Regulation of Interleukin–6, Osteoclastogenesis, and Bone Mass by Androgens, J. Clin. Invest. 95:2886–2895 (1995).

Bellido, T. et al. Activation of the Janus Kinase/STAT (Signal Transducer and Activatior of Transcription) Signal Transduction Pathway by Interleukin–6–Tye Cytokines Promotes Osteoblast Differentiation, Endocrinology 138:3666–3676 (1997).

Berggren, M. et al. Glutathione Biosynthesis in the Isolated Perfused Rat Lung: Utilization of Extracellular Glutathione, Federation European Bicohemcal Societies, 176: 189–192 (1984).

Boyce, R.W. et al. The Effects of Risedronate on Canine Cancellous Bone Remodeling: Three–Dimensional Kinetic Reconstruction of the Remodeling Site, J. Bone Miner. Res. 10:211–221 (1995).

Brown, R.J. et al. Differential Effects of Aminosubstituted Analogs of Hydroxy Bisphosphonates on the Growth of *Dictyostelium discoideum*. Journal of Bone and Mineral Research 13:253–258 (1998).

Bursch, W. et al. Determination of the length of the histological stages of apoptosis in normal liver and in altered hepatic foci of rats, Carcinogenesis 11:847–853 (1990).

Chauhan, D. et al. Dexamethasone induces apoptosis of multiple myeloma cells in a JNK/SAP kinase independent mechanism, Oncogene 15:837–843 (1997).

Chavassieux, P.M. et al. Histomorphometeric Assessment of the Long–term Effects of Alendronate on Bone Quality and Remodeling in Patients with Osteoporosis, J. Clin. Invest. 100:1475–1480 (1997).

Clevenger, C.V. et al. Role of Bag–1 in the Survival and Proliferation of the Cytokine–Dependent Lymphocyte Lines, Ba/F3 and Nb2, Mol. Endocrinology. 11:608–618 (1997).

Cummings, SR et al. Changes in BMD Substantially Underestimate the Anti–Fracture Effects of Alendronate and Other Antiresorptive Drugs. Journal of Bone and Mineral Research 11(Suppl):S102 (1996)(Abstract).

Dempster, D.W., Exploiting and Bypassing the Bone Remodeling Cycle to Optimize The Treatment of Osteoporosis, Journal of Bone and Mineral Research. 12:1152–1154 (1997).

Dempster, D.W., New Concepts in Bone Remodeling In: Dynamics of Bone and Cartilage Metabolism (1999) 261–273 Academic Press.

Duncan, R.L. et al. Calcif. Tissue Int. 57:344 (1995).

Ellis, E. F. et al., Restoration of cerebrovascular responsiveness to hyperventilation by the oxygen radical scavenger n–acetylcysteine following experimental traumatic brain injury, Journal of Neurosurgery. 75:774–779 (1991).

Ettinger, B. et al., Reduction of Vertebral Fracture Risk in Postmenopausal Women With Osteoporosis Treated with Raloxifene, Journal of the American Medical Association. 282:637–645 (1999).

Falcini, F. et al., Intravenous Administration of Alendronate Counteracts the In Vivo Effects of Glucocorticoids on Bone Remodeling, Calcified Tissue International. 58:166–169 (1996).

Farley, J.R. et al., Calcitonin Has Direct Effects of 3[H]–Thymidine Incorporation and Alkaline Phosphatase Activity in Human Osteoblast–Line Cells, Calcified Tissue International. 48:297–301 (1991).

Favata, M.F. et al, Identification of a Novel Inhibitor of Mitogen–activated Protein Kinase Kinase, The Journal of Biological Chemistry. 273:18623–18632 (1998).

Ferretti, J.L. et al. Calcif. Tissue Int. 57:399 (1995).

Fitzpatrick, L.A. Selective Estrogen Receptor Modulators and Phytoestrogens: New Therapies for the Postmenaopausal Women Mayo Clin. Proc. 74:601–607 (1999).

Fleish, H., Bisphosphonates in Bone Disease: From the Laboratory to the Patient, The Parathenon Publishing Group (1995).

Forrest, S.M. et al. Characterization of an osteoblast–like clonal cell line which responds to both parathyroid hormone and calcitonin. Calcif. Tissue Int. 37:51–56 (1985).

Frost, H.M. Bone 20:385 (1997).

Gardner, A.M. and Johnson, G.L., Fibroblast Growth Factor–2 Suppression of Tumor Necrosis Factor a–Mediated Apoptosis Requires Ras and the Activation of Mitogen–activated Protein Kinase, The Journal of Biological Chemistry. 271:14560–14566 (1996).

Giuliani, N. et al., Alendronate stimulates b–FGF production and mineralized nodule formation in human osteoblastic cells and osteoblastogenesis in human bone marrow cultures. Journal of Bone Mineral Research 10(Suppl):S171 (Abstract) (1995).

Giuliani, N. et al., Bisphosphonates Stimulate Formation of Osteoblast Precursors and Mineralized Nodules in Murine and Human Bone Cultures in Vitro and Promote Early Osteoblastogenesis in Young and Aged Mice In Vivo, Bone. 22:455–461 (1998).

Glorieux, F.H. et al., Cyclic Administration of Pamidronate in Children with Severe Osteogenesis Imperfecta, New England Journal of Medicine. 399:947–952 (1998).

Gonnelli, S. et al., Prevention of Corticosteroid–Induced Osteoporosis with Alendronate in Sarcoid Patients, Calcified Tissue International. 61:382–385 (1997).

Grignani, F. et al., High–Efficiency Gene Transfer and Selection of Human Hematopoietic Progenitor Cells with a Hybrid EBV/Retroviral Vector Expressing the Green Fluorescence Protein, Cancer Research. 58:14–19 (1998).

Hughes, D.E. et al., Estrogen promotes apoptosis of murine osteoclasts mediated by TGF–, Nature Medicine. 2:1132–1136 (1996).

Hughes, D.E. et al., Inhibition of Osteoclast–like Cell Formation by Bisphosphonates in Long–term Cultures of Human Bone Marrow, Journal of Clinical Investigation. 83:4–6:1930–1935 (1989).

Hughes, D.E. et al., Bisphosphonates Promote Apoptosis in Murine Osteoclasts In Vitro and In Vivo, Journal of Bone and Mineral Research. 10:1478–1487 (1995).

Ilda–Klein, A. et al., Effects of Calcitonin on 3', 5'–Cyclic Adenosine Monophosphate and Calcium Second Messenger Generation and Osteoblast Function in UMR 106–06 Osteoblast–Like Cells, Endocrinology. 130:381–388 (1992).

Jilka, R.L. et al, Increased Osteoclast Development After Estrogen Loss: Mediation by Interleukin–6, Science 257:88–91 (1992).

Jilka, R.L. et al., Osteoblast Programmed Cell Death (Apoptosis): Modulation by Growth Factors and Cytokines, Journal of Bone and Mineral Research. 13:793–802 (1998).

Jilka, R.L. et al., Linkage of Decreased Bone Mass with Impaired Osteoblastogenesis in a Murine Model of Accelerated Senescence. The Journal of Clinical Investigation. 97:1732–1740 (1996).

Jilka, R.L. et al., Loss of Estrogen Upregulates Osteoblastogenesis in the Murine Bone Marrow, Evidence of Autonomy from Factors Released during Bone Resorption, The American Society for Clinical Investigation, Inc. 101:1942–1950 (1998).

Jilka, R.L. et al., Increased bone formation by prevention of osteoblast apoptosis with parathyroid hormone, The Journal of Clinical Investigation. 104:439–446 (1999).

Kalderon, B.L., A Short Amino Acid Sequence Able to Specify Nuclear Location, Cell. 39:499–509 (1984).

Kato, Y. et al., Establishment of an Osteocyte–like Cell Line, MLO–Y4, Journal of Bone and Mineral Research. 12:2014–2023 (1997).

Kleiber, M. The Fire of Life: An Introduction to Animal Energetics. John Wiley & Sons, Inc. New York. Chapters 10:177–216 and 11:217–230 (1961).

Knight, K.R. et al., Enhancement of ischaemic rabbit skin flap survival with the antioxidant and free–radical scavenger N–acetylcysteine, Clinical Science. 81:31–36 (1991).

Lalitha, T. et al., Effect of N–Acetyl–cysteine, D–Penicillamine and Buthionine Sulfoximine on Glutathione Levels and CNS Oxygen Toxicity in Rats, Pharmacology & Toxicology. 66:56–61 (1990).

Luckman, S.P. et al., Nitrogen–Containing Bisphosphonates Inhibit the Mevalonate Pathway and Prevent Post–Translational Prenylation of GTP–Binding Proteins, Including Ras, Journal of Bone and Mineral Research. 13:581–589 (1998).

Machwate, M. et al., Shingosine Kinase Mediates Cyclic AMP Suppression of Apoptosis in Rate Periosteal Cells, Molecular Pharmacology. 54:70–77 (1998).

Manolagas, S.C. et al., Bone Marrow, Cytokines, and Bone Remodeling: Emerging Insights into the Pathophysiology of Osteoporosis, New England Journal of Medicine. 332:305–311 (1995).

Manolagas, S.C. et al., Opposite Effects of Estrogen on the Life Span of Osteoblasts/Osteocytes Versus Osteoclasts In Vivo and In Vitro: An Explanation of the Imbalance between Formation and Resorption in Estrogen Deficiency, Journal of Bone and Mineral Research 14:S169 (1999) (Abstract).

Marotti, G. The Structure of Bone Tissues and the Cellular Control of Their Deposition, Ital. J. Anat. Embryol. 101:25–79 (1996).

Marotti, G. et al., Structure–function relationships in the osteocyte, Italian Journal of Mineral & Electrolyte Metabolism. 4:93–106 (1990).

Mullender, M.G. et al. Bone 20:527 (1997).

Nijweide, P.J. et al., The Osteocyte, In: Principles of Bone Biology. Chap 9:115–126 (1996) Academic Press, San Diego.

Nishikawa, M. et al., Bisphosphonates Act on Osteoblastic Cells and Inhibit Osteoclast Formation in Mouse Marrow Cultures, Bone. 18:9–14 (1996).

Noble, B.S. et al., Identification of Apoptotic Changes in Osteocytes in Normal and Pathological Human Bone, Bone. 20:273–282 (1997).

Papapoulous, S.E., Bisphosphonates, Pharmacology and Use in the Treatment of Osteoporosis, Osteoporosis. In: Osteoporosis, Chap 64:1209–1234 (1996) Academic Press, San Diego.

Parfitt, A.M., Bone–Forming Cells in Clinical Conditions In:Bone vol. 1 The osteoblast and osteocyte. 351–430 (1996) CRC Press, Boca Raton.

Parfitt, A.M. et al., A New Model for the Regulation of Bone Resorption with Particular Reference to the Effects of Bisphosphonates, Journal of Bone and Mineral Research 11:150–159 (1996).

Peel, N.F.A. et al., Risk of vertebral fracture and relationship to bone mineral density in steroid treated rheumatoid arthritis, Annals of the Rheumatic Diseases. 54:801–806 (1995).

Plotkin, L.I. et al., Bisphosphonates Prevent Glucocorticoid–Induced Apoptosis of Osteocytes In Vitro: a Putative Mechanism Influencing Mechanosensing, Bone. 23:S157 (1998).

Plotkin, L.I. et al. Prevention of osteocyte and osteoblast apoptosis by biphosphonates and calcitonin. Journal of Clinical Investigation 104:1363–1374 (1999).

Pompeiano, M. et al. Onset of apoptotic DNA fragmentation can precede cell elimination by days in the small intestine Cell Death and Differentiation 5:702–709 (1998).

Reichardt, H.M. et al., DNA Binding of the Glucocorticoid Receptor Is Not Essential for Survival, Cell. 93:531–541 (1998).

Reid, I.R. et al., Prevention of Glucocorticoid–Induced Osteoporosis, Journal of Bone and Mineral Research. 5::619–623 (1990).

Rodan, G.A. and Fleisch, H.A. Bisphosphonates: Mechanisms of Action, The Journal of Clinical Investigation. 97:2692–2696 (1996).

Sahni, M. et al. Bisphosphonates act on rat bone resorption through the mediation of osteoblasts. Journal of Clinical Investigation 91:2004–2011 (1993).

Sakagami, Y. et al., Stimulation of Interleukin–6 Production by Either Calcitonin Gene–Related Peptide or Parathyroid Hormone in Two Phenotypically Distinct Bone Marrow–Derived Murine Stromal Cell Lines, Journal of Bone and Mineral Research. 8:811–816 (1993).

Schlegel, J. et al., CPP32/Apopain Is a Key Interleukin 1 Converting Enzyme–like Protease Involved in Fas–mediated Apoptosis: The Journal of Biological Chemistry. 271:1841–1844 (1996).

Smilkstein, M.J. et al., Efficacy of Oral N–Acetylcysteine in the Treatment of Acetaminophen Overdose, The New England Journal of Medicine. 319:1557–1562 (1988).

Snyder, P.J. et al., Effect of Testosterone Treatment on Bone Mineral Density in Men Over 65 Years of Age J. Clin. Endocrin. Metab. 84: 1966–1972 (1999).

Stefanelli, C. et al., Inhibition of etoposide–induced apoptosis with peptide aldehyde inhibitors of proteasome, Biochemical Journal. 332:661–665 (1998).

Storm, T. et al., Changes in Bone Histomorphometry After Long–Term Treatment with Intermittent, Cyclic Etidronate for Postmenopausal Osteoporosis, Journal of Bone and Mineral Research. 8:199–208 (1993).

Tenebaum, H.C. et al., Effects of Bisphosphonates and Inorganic Pyrophosphate on Osteogenesis in Vitro, Bone. 13:249–255 (1992).

Thornberry, N.A. and Lazebnik, Y., Caspases: Enemies Within, Science. 281:1312–1316 (1998).

Turner, C.H. et al. Bone 22:463 (1998).

Van Beek, E. et al., Dissociation of Binding and Antiresorptive Properties of Hydroxbisphosphonates by Substitution of the Huydroxyl with an Amino Group, Journal of Bone and Mineral Research. 11:1492–1497 (1996).

Verheijen, M.H. and Defize, L.H. Parathyroid hormone activates mitogen–activated protein kinase via cAMP–mediated pathway independent of Ras. Journal of Biological Chemistry 272:3423–3429 (1997).

Vitte, C. et al., Bisphosphonates Induce Osteoblasts to Secrete an Inhibitor of Osteoclast–Mediated Resorption, Endocrinology. 137:2324–2333 (1996).

Wang, X. et al., The cellular response to oxidative stress: influences of mitogen–activated protein kinase signalling pathways on cell survival, Biochemical Journal. 333:291–300 (1998).

Weinstein, R.S. et al., The Effects of Androgen Deficiency on Murine Bone Remodeling and Bone Mineral Density are Mediated via Cells of the Osteoblastic Lineage, Endocrinology. 138:4013–4021 (1997).

Weinstein, R.S. et al., Inhibition of Osteoblastogenesis and Promotion of Apoptosis of Osteoblasts and Osteocytes by Glucocorticoids, The Journal of Clinical Investigation. 102:274–282 (1998).

Weinstein, S. et al., Anatomic Juxtaposition of Apoptotic Osteocytes and Avascular Necrosis in Femurs from Patients with Glucocorticoid Excess, Bone. 23:S461 (1998).

Xia, Z. et al., Opposing Effects of ERK and JNK–p38 MAP Kinases on Apoptosis, Science. 270:1326–1331 (1995).

* cited by examiner

INCREASING BONE STRENGTH WITH SELECTED BISPHOSPHONATES

CROSS-REFERENCE TO RELATED APPLICATION

This application claims benefit of priority of U.S. provisional application Ser. No. 60/109,237, filed Nov. 19, 1998, and U.S. provisional application Serial No. (60/165,480), filed on Nov. 15, 1999 by Stavros Manolagas and Teresita Bellido, entitled "Increasing Bone Strength via Decreased Osteocyte/Osteoblast Apoptosis."

FEDERAL FUNDING LEGEND

This invention was produced in part using funds obtained through grant PO1AG/AMS13918, AR43003, AR46191 and AR43453 from the National Institutes of Health. Consequently, the federal government has certain rights in this invention.

FIELD OF THE INVENTION

The present invention is in the field of bone physiology and morphology, and specifically, describes the identification and use of selected bisphosphonates and calcitonin derivatives to increase bone mass which (i) inhibit the apoptosis of osteocytes and/or osteoblasts (ii) without substantially affecting the activity of osteoclasts.

BACKGROUND OF THE INVENTION

Bones consist of living cells embedded within a matrix of proteins and minerals. Bones provide support and protection to the vital organs of the animal, and give strength and form to its structure. Diseases of the bone, therefore, may have significant deleterious effects on humans as well as other vertebrates.

Osteoporosis is a decrease in bone mass in combination with microarchitectural deterioration which leads to bone fragility and fractures. Treatments for osteoporosis have historically focused on the prevention of further bone loss. In contrast, a bone anabolic agent is one that substantially increases bone mass. An increase in bone mass does not necessarily lead to a decrease in bone fragility. To date, while there have been several drugs approved by the U.S. Food and Drug Administration for the treatment of osteoporosis, it is believed that no drug has yet been approved in the United States to be used as a bone anabolic agent, for either humans or other animals.

Bone is a dynamic tissue which undergoes continual resorption and formation through a remodeling process, which is accomplished by two types of cells: osteoclasts, which erode cavities, and osteoblasts that synthesize new bone matrix. Remodeling takes place mainly on the internal surfaces of bone and it is carried out not by individual cells, but rather by temporary anatomical structures, termed basic multi-cellular units (BMUs), comprising teams of osteoclasts in the front and osteoblasts in the rear. In an established BMU, bone resorption and formation happens at the same time.

After osteoclasts stop resorbing bone, they die by apoptosis and are quickly removed by phagocytes. During the longer lifespan of the osteoblasts (about three months, as compared to three weeks for osteoclasts), some osteoblasts convert to lining cells that cover quiescent bone surfaces and some are entombed within the mineralized matrix as osteocytes (Parfitt, In: Bone, Telford and CRC Press, PP351–429, 1990). However, the majority (65%) of osteoblasts that originally assembled at the remodeling site die by apoptosis (Jilka et al., JBMR 13:793–802, 1998).

Osteocytes are the most abundant bone cell type and are buried deep in the mineralized bone matrix within lacunae connected with canaliculi through which the long and slender cytoplasmic processes of osteocytes are connected with neighboring osteocytes and with the cells on the bone surface and of the bone marrow.

Because of their sheer number, regular spacing throughout the mineralized matrix and their anatomical connections with other bone cells, osteocytes are believed to be the sensors of the local need for bone augmentation or reduction during functional adaptation of the skeleton, the detection of microdamage, and the transmission of signals that lead to bone repair by remodeling. Specifically, it is thought that mechanical strains on bone cause deformations that result in flow of fluid within the osteocytic lacunae and canaliculi. The changes in fluid flow are sensed by the osteocytes, which, in turn, transmit signals to osteoblasts (new bone-forming cells) and osteoclasts (old bone-removing cells). Osteoblasts and osteoclasts react by remodeling the mineral tissue so that it is permanently adapted to daily mechanical deformations. When this system fails, the tissue becomes fragile, and bone structure proves inadequate and brittle.

Bone fragility is a pathologic condition that may be caused by various factors, including a poor quality of mineralized tissue or more usually by weak structure, unable to respond competently to the customary mechanical requirements of the skeleton. Poor osteocytic activity is related to this state of fragility (Duncan R L et al., *Calcif. Tissue Int.* 1995, 57:344; Mullender M G et al., *Bone* 1997, 20:527; Turner C H et al., *Bone* 1998, 22:463). The bone structures that jointly constitute the human skeleton and that of vertebrate animals are permanently distorted by the application of external forces, in which muscular force usually intervenes (Ferretti J L et al., *Calcif. Tissue Int.* 1995, 57:399; Frost H M, *Bone* 1997, 20:385). Consistent with the critical role of osteocytes in bone maintenance, it has recently been demonstrated that glucocorticoid excess, traditionally a cause of severe boneloss and osteonecrosis leading to the collapse of joints, dramatically increases osteocyte and osteoblast apoptosis (Weinstein et al., *J. Clin. Invest.*, 102:274); whereas, intermittent administration of parathyroid hormone, a method of anabolic bone therapy, has the opposite effect on osteocyte and osteoblast apoptosis (Jilka et al., *J. Clin. Invest.*, 104:439–446, 1999).

Most metabolic disorders of the adult skeleton result from an imbalance between the resorption of old bone by osteoclasts and its subsequent replacement by osteoblasts. Changes in cell numbers, opposed to individual cell activity (Manolagas and Jilka, NEJM 332:305–311, 1995), appears to be the cause of most metabolic bone diseases, including the three most common forms of osteoporosis: osteoporosis due to sex steroid deficiency in females and males (Jilka et al., Science 257:88–91, 1992; Jilka et al., JCI 101:1942–1950, 1998; Bellido et al., JCI 95:2886–2895, 1995; Weinstein et al., Endocrinology 138:4013–4021, 1997); osteoporosis due to old age (Jilka et al., JCI 97:1732–1740, 1996); and osteoporosis due to glucocorticoid-excess (Weinstein et al., JCI 102:274–282, 1998; Weinstein et al., Bone, 23:S461, 1998; Bellido et al., Bone, 23:S324, 1998). Structural bone alterations caused by decreased osteocyte life span predisposes the bone to irreversible deformations and fractures. This condition is designated "skeletal fragility."

Agents that reduce bone turnover by inhibiting remodeling (commonly but inaccurately referred to as "antiresorptive") increase bone mass by a maximum of 6–10%, and more typically, 2–3%, as measured by Dual Energy X-Ray Absorptiometry (DEXA). Most of this increase is in the first 1–2 years and is due to contraction of the remodeling space. Modest further increases may result from more complete secondary mineralization. Improvement of focal balance due to reduction of resorption depth has been demonstrated in animal experiments, but not yet in human subjects. Regardless of the mechanism, an increase of less than 10% will in almost all cases fail to restore bone mass to its peak value and fail to reestablish trabecular connectivity so that fracture risk will remain increased.

Over the past three decades, bisphosphonates (BP's), stable analogs of pyrophosphate and calcitonin have been developed as potent inhibitors of bone resorption and effective agents for the management of osteoporosis and other bone diseases (Fleisch, H. 1997. Bisphosphonates in bone disease. From the laboratory to the patient. The Partenon Publishing Group Inc., One Blue Hill Plaza, New York 10965, USA.; Papapoulos, S. 1996. Bisphosphonates. Pharmacology and use in the treatment of osteoporosis. In Osteoporosis. R. Marcus, D. Feldman, and J. Kelsey, editors. Academic Press, San Diego, Calif. 1209–1234 Rodan, G. A. and H. A. Fleisch. 1996. *J. Clin. Invest.* 97:2692–2696; Azria, et al., 1996. Calcitonin. In Principles of Bone Biology. J. P. Bilezikian, et al., eds, Academic Press, San Diego, Calif. 1083–1097). Decreased osteoclast progenitor development, decreased osteoclast recruitment, and promotion of apoptosis of mature osteoclasts leading to decreased bone remodeling are thought to be the main mechanisms of the antiresorptive actions of BPs (Hughes, et al., 1995. *J. Bone Miner. Res.* 10:1478–1487; Hughes, et al., 1989. *J. Clin. Invest.* 83:1930–1935; Parfitt, et al., 1996. *J. Bone Miner. Res* 11:150–159). Likewise, disruption of osteoclast function is the main mechanism for the antiresorptive actions of calcitonin (Azria, et al., 1996. Calcitonin. In Principles of Bone Biology. J. P. Bilezikian, et al., eds, Academic Press, San Diego, Calif. 1083–1097). At least some of the effects of BPs on osteoclast development and function might be mediated indirectly through actions on cells of the osteoblastic lineage. Thus, pretreatment of osteoblastic cells with BPs inhibits the formation of osteoclast-like cells from their marrow or spleen precursors (Nishikawa, et al., 1996. *Bone* 18:9–14), as well as osteoclast resorbing activity in concultures with mature osteoclasts (Sahni, et al., 1993. *J. Clin. Invest.* 91:2004–2011; Vitte, et al., 1996. *Endocrinology* 137:2324–2333). These inhibitory effects can be reproduced by addition of conditioned media from BP-treated osteoblastic cells to the cultures, suggesting that BPs promote the release of factors that inhibit osteoclast formation and activity (Nishikawa, et al., 1996. *Bone* 18:9–14; Sahni, et al., 1993. *J. Clin. Invest.* 91:2004–2011; Vitte, et al., 1996. *Endocrinology* 137:2324–2333).

Long-term treatment of human and nonhuman primates with BPs increases wall thickness, an index of focally increased osteoblast numbers or activity, resulting in more complete refilling of resorption cavities (Chavassieux, et al., 1997. *J. Clin. Invest.* 100:1475–1480; Storm, et al., 1993. *J. Bone Miner. Res.* 8:199–208.). This evidence has raised the possibility that BPs do more than simply reduce remodeling space and that they may possess anabolic activity (Giuliani, et al., 1998. *Bone* 22:455–461).

Antiresorptive agents such as BPs and calcitonin, as well as estrogen, decrease fracture incidence disproportionally to their effect on bone mass (Cummings, et al., 1996. *J. Bone Miner. Res.* 11 (suppl):S102(Abstr.)). This suggests an additional effect on bone strength unrelated to effects on bone mineral density (BMD). However, an explanation for this phenomenon has remained elusive. Osteocytes, differentiated osteoblasts regularly spaced throughout the mineralized matrix, are believed to detect bone microdamage and to transmit signals leading to its repair (Marotti, et al., 1990. *Ital. J. Min. Electrol. Metab.* 4:93–106; Nijweide et al., 1996, The osteocyte, Principles of Bone Biology, Bilezikian, et al. editors, Academic Press, San Diego, Calif. 115–126.). Disruption of the osteocyte network might compromise this mechanism, leading to microdamage accumulation and increased bone fragility. Such a defect in bone quality might account for the higher incidence of fractures in glucocorticoid-treated patients compared with postmenopausal women, even though BMD in the former is relatively higher (Peel, et al., 1995. *Ann. Rheum. Dis.* 54:801–806; Dennison, E. 1999. Epidemiology of glucocorticoid-induced osteoporosis. *Osteoporosis Int.* 9:S16(Abstr.)). There have been observations that glucocorticoid excess increases the prevalence of osteocyte and osteoblast apoptosis (Weinstein, et al., 1998. *Bone* 23(suppl):S461(Abstr.); Weinstein et al., 1998. *J. Clin. Invest.* 102:274–282). and that BPs are effective in the management of this condition (Reid, et al., 1990. *J. Bone Miner. Res.* 5:619–623; Gonnelli, et al., 1997. *Calcif. Tissue Int.* 61:382–385; Falcini, et al. 1996. *Calcif. Tissue Int.* 58:166–169).

The currently approved treatments for osteoporosis focus on inhibiting osteoclastic bone resorption. Inhibition of osteoclastic bone resorption causes less removal of "old" mineral tissue and avoids excessive losses of calcified structures, such as those which occur in certain skeletal diseases, particularly osteoporosis. Although treatment with bisphosphonates allows for preservation of a greater quantity of skeletal mass, such withholding may slow down or disturb the adjustment of the skeleton by "freezing" tissue renewal. Moreover, by means of the anti-osteoclast treatment, incompetent mineralized structures may be preserved and thus cause "fatigue" to the neighboring structures. "Fatigue" happens with all overburdened material structures, paradoxically increasing the risk of fracture.

Approved therapeutic agents for osteoporosis, such as bisphosphonates, estrogen and calcitonin, are believed to exert their beneficial effects by inhibiting osteoclastic bone resorption. There are currently ten classes of drugs that are used in the treatment of osteoporosis: anabolic steroids, bisphosphonates, calcitonins, estrogens/progestogens, Selective Estrogen Receptor Modulators (SERMs) such as raloxifene and phytoestrogen, parathyroid hormone ("PTH"), fluoride, Vitamin D metabolites, and calcium preparations. No compound within these classes has been approved as a bone anabolic agent.

Anabolic Steroids (Androgens)

Anabolic steroids (androgens) have bee n known to build muscle mass in the host. However, there has been no reported evidence that they function as bone anabolic agents as defined herein (Snyder et al., JCEM 84:1966–1972, 1999). Androgens are typically used as a replacement therapy for male hypogonadal disorders and they are used in adolescent males with a history of delayed puberty or growth. Androgens can produce significant side effects when taken over a period of time, including water retention, jaundice, decreased high density lipoprotein and increased low density lipoprotein, hepatic toxicity (most usually associated with the 17α-alkylated androgens), hepatic carcinoma, increased risk of cardiovascular disease, and when taken in large dosages, irrationality, psychotic episodes, violent behavior, and death. U.S. Pat. No. 5,565, 444 discloses the use of an androgen for the treatment of bone loss or for increasing bone mass.

Calcitonin

Endogenous calcitonin is a polypeptide hormone involved in the regulation of calcium and bone metabolism. Forms used therapeutically include calcitonin (pork), extracted from pig thyroid, a synthetic human calcitonin; elcatonin, a synthetic analogue of eel calcitonin; and salcatonin, a synthetic salmon calcitonin. They all have the property of lowering plasma-calcium concentration by diminishing the rate of bone resorption. Calcitonins are typically administered subcutaneously or by intramuscular injection.

Bisphosphonates

Bisphosphonates, as stated above, have been widely used to treat osteoporosis. The bisphosphonate disodium etidronate has similar effects on bone mass and fractures in established osteoporosis to those of calcitonin, but cannot be given for a prolonged period because of the risk of osteomalacia. Bisphosphonate alendronate treatment at a dose of 10 mg/day results in a 5% increase in spinal bone mineral density (BMD) over the first year (Dempster, Exploiting and Bypassing the Bone Remodeling Cycle to Optimize the Treatment of Osteoporosis, Journal of Bone and Mineral Research, Volume 12, Number 8, 1997, pages 1152–1154). BMD continues to increase, albeit at a slower rate, at this site during the second and third years of treatment. The magnitude and duration of the increase in BMD has led to speculation that alendronate is doing more than simply reducing remodeling space and that it may possess anabolic activity. The bisphosphonate etidronate reduced resorption depth in human iliac trabecular bone by almost 30% after one year of treatment, but no such data are yet available for alendronate. Etidronate did not change the thickness of trabecular packets, but recent studies in osteoporotic women suggest that this is increased after two years of alendronate treatment at 10 and 20 mg/day. This result was not confirmed after three years of treatment.

In another article, Dempster (Dempster D. W., New concepts in bone remodeling, In: Dynamics of Bone and Cartilage Metabolism, Chapter 18, pp. 261–273, Acad. Press, 1999) confirms that the potential for an agent that can increase bone mass and hence reverse the skeletal defect in patients with osteoporosis is great, particularly if in doing so it also repairs microarchitectural damage. He notes that estrogens and calcitonin primarily stabilize bone mass and prevent further loss of bone, although a transient small increment in mass is often reported, particularly in patients with elevated levels of bone remodeling. Dempster et al. conclude that this is not a true anabolic effect but is related to the temporal effects on turnover in which resorption declines initially followed by a reduction in formation that may take several months.

It was disclosed in the priorty document to this application, for the first time, that that bisphosphonates have anti-apoptotic effects on osteoblasts and osteocytes. This fundamental discovery has been published by the inventors after the priority date in Plotkin et al. *Bone*, 23:S157, 1998; *J. Clin. Invest*; 104:1363–1374, 1999. Significantly, the anti-apoptotic effect of bisphosphonates in vitro is achieved with doses 100–1000 lower than the doses at which these same agents inhibit osteoclast activity; and additionally can be demonstrated with bisphosphonates that do not block osteoclast activity at all (compound IG9204).

U.S. Pat. No. 4,870,063 discloses a bisphosphonic acid derivative to increase bone mass.

U.S. Pat. Nos. 5,532,226 and 5,300,687 describe the use of trifluoromethylbenzylphosphonates to increase bone mass.

U.S. Pat. No. 5,885,973 to Papapoulos, et al., discloses a bone mass anabolic composition that includes olpandronate, which is a bisphosphonate.

WO 97/02827 filed by Gador S. A. and the University of Leiden discloses 1-amino-3-(N,N-dimethylamino)-propyliden-1,1-bisphosphonic acid (referred to sometimes as "IG9402") acid as a carrier for bone active substances or for the preparation of a medicament for the diagnosis, prophylaxis and/or mineral metabolism disorders. WO 97/02827 discloses on page 5 that IG9402, illustrated below, is devoid of any antiresorptive activity, which is used as the basis for the essential feature of that disclosed invention. The application does not provide an explanation for why this specific bisphosphonate does not have antiresorptive activity, which has been considered the classic mechanism of action of bisphosphonates.

Estrogens/Progestogens

Estrogens/progestogens (anti-remodeling and anti-resorptive compounds) as a class have not to date been shown to increase bone mass by more than 10%, but instead have been used to retard the effect of osteoporosis. Estrogens are currently the most effective method of preventing osteoporosis in postmenopausal women.

U.S. Pat. No. 5,183,815 discloses the use of a steroidal hormone covalently linked to a hydroxy alkyl-1,1-bisphosphonate.

U.S. Pat. No. 5,843,934 claims that an estrogen having insubstantial sex-related activity can be administered to a patient to retard the adverse effects of osteoporosis in a male or female. The '934 patent does not address how to select a compound to increase bone mass, but instead teaches how to retard the effect of bone loss.

WO 98/22113 filed by the University of Florida Research Foundation, Inc. discloses methods to utilize an α or β-isomer of an estrogen compound to confer cytoprotection on a population of cells associated with an ischemic event.

Phytoestrogen

Little is known about the actions of phytoestrogens on bone (Fitzpatrick, L. A., Mayo Clinic Proceedings, 74:601–607, 1999). Soy protein did not prevent increased bone turnover in cynomolgus monkeys; they actually increased it. However, BMD declined after two years in postmenopausal women taking only calcium but did not change in those receiving ipriflavone. Isoflavone significantly increased spinal BMD in postmenopausal women after 6 months of 40 mg/day of soy protein supplementation (containing 90 mg isoflavones) but not with lower doses (56 mg/day) (Feinkel, E. Lancet, 352:762, 1998).

Parathyroid Hormone (PTH)

Daily injections of parathyroid hormone (PTH), an agent known for its role in calcium homeostasis, increases bone mass in animals and humans, as does the related PTH-related hormone PHTrP, the only other known ligand of the PTH receptor. Whereas increased prevalence of apoptosis of osteoblasts and osteocytes are key pathogenic mechanisms for steroid-induced osteoporosis (Weinstein et al., J Clin Invest, 102:274–282, 1998; Weinstein et al., Bone, 23:S461, 1998; Bellido et al., Bone, 23:S324, 1998), the reverse, i.e., postponement of osteoblast apoptosis, is the principal, if not the sole, mechanism for the anabolic effects of intermittent parathyroid hormone administration on bone (Jilka et al., J. Clin. Invest. 104:439–446 1999). The increased bone mineral density, osteoblast perimeter and bone formation rate that occur with intermittent PTH administration in mice happen without a change in osteoblast production. Instead, the anabolic effect of the drug is due to decreased prevalence of osteoblast apoptosis from 1.7–2.2% to as little as 0.1–0.4%, while the osteocytes in the newly made lamellar cancellous bone are closer together and more numerous than those found in the animals receiving vehicle alone. The closely spaced, more numerous osteocytes are the predictable consequence of protecting osteoblasts from apoptosis. The anti-apoptotic effect of PTH on osteoblasts as well as osteocytes has been confirmed in vitro using primary bone cell cultures and established cell lines.

The use of teriparatide (the 1–34 amino acid fragment of human parathyroid growth hormone) to stimulate bone formation has also been investigated; teriparatide administered as daily injections has been reported to selectively increase the trabecular bone density of the spine in osteoporotic patients.

U.S. Pat. No. 5,510,370 discloses the use of a combination of PTH and raloxifene to increase bone mass. U.S. Pat. No. 4,833,125 discloses the use of PTH in combination with either a hydroxylated vitamin D derivative, or a dietary calcium supplement.

Calcium Preparations

Calcium preparations, while useful as a dietary supplement for persons who are calcium deficient, have not been shown effective to increase bone mass. However, they may reduce the rate of bone loss. U.S. Pat. No. 5,618,549 (a calcium salt) describes the use of calcium.

Fluoride

The most thoroughly studied anabolic agent, sodium fluoride, can increase vertebral bone mass by 10% a year for at least four years but there is controversy about the quality of the bone formed. Sodium fluoride has not been approved as a bone anabolic agent. It has been difficult to establish anti-fracture efficacy because of serious qualitative abnormalities. First, much of the new bone is initially woven rather than lamellar. Second and more important, there is severe impairment of bone mineralization, in spite of sodium fluoride's effectiveness in increasing bone mass.

U.S. Pat. No. 5,071,655 discloses a composition to increase bone mass that includes a fluoride source and a mitogenic hydantoin.

SERMs

SERMs such as tamoxifen and raloxifene have also been used to treat osteoporosis. A recent study carried out with raloxifene indicated that after three years of treatment, women on raloxifene had 30–50% fewer spinal fractures, and had 2–3% increase in bone density in their hips and spine, but showed no fewer nonspinal fractures, a category that includes hip fractures (Ettinger, B., JAMA, 282:637–645, 1999).

U.S. Pat. No. 4,970,237 discloses the use of clomiphene to increase bone mass in premenopausal women.

Vitamin D Derivatives

There have been conflicting reports about the value of Vitamin D or its derivatives on bone loss and bone anabolism. Some studies on the hormonal metabolite of vitamin D, calcitriol, have reported an increase in spinal bone density, but others have found no effect.

The following patents describe the use of Vitamin D derivatives to treat bone disease: U.S. Pat. Nos. 4,973,584; 5,7507,46; 5,593,833; 5,532,391; 5,414,098; 5,403,831; 5,260,290; 5,104,864; 5,001,118; 4,973,584; 4,619,920; and 4,588,716.

Other Compounds

The following patents disclose the use of other compounds for the treatment of bone disease: U.S. Pat. Nos. 5,753,649 and 5,593,988 (azepine derivative); 5,674,844 (morphogen); 5,663,195 (cyclooxygenase-2 inhibitor); 5,604,259 (ibuprofen or flurbiprofen); 5,354,773 (bafilomycine); 5,208,219 (activin); 5,164,368 (growth hormone releasing factor); and 5,118,667, 4,870,054 and 4,710,382 (administration of a bone growth factor and an inhibitor of bone resorption).

U.S. Pat. No. 5,859,001 discloses the use of non-estrogen compounds having a terminal phenol group in a four-ring cyclopentanophenanthrene compound structure to confer neuroprotection to cells.

U.S. Pat. No. 5,824,672 discloses a method for preserving tissues during transplantation procedures that includes administering an effective dose of a cyclopentanophenanthrene compound having a terminal phenol A ring.

WO 98/31381 filed by the University of Florida Research Foundation, Inc. discloses a method for enhancing the cytoprotective effect of polycyclic phenolic compounds on a population of cells that involves the steps of administering a combination of polycyclic phenolic compounds and antioxidants to achieve an enhanced effect. One disclosed combination is glutathione and estrogen.

It is an object of the present invention is to provide methods of screening for compounds to increase bone strength.

It is another object of the present invention to provide compounds and compositions to increase bone strength in patients in need thereof.

SUMMARY OF THE INVENTION

The present invention is a method and composition to increase bone strength in a manner that decreases fracture incidence, which may or may not include increasing bone mineral density ("BMD"). The invention includes administering an effective amount of a bisphosphonate to a host in need thereof to increase bone strength, which inhibits the apoptosis of osteoblasts and osteocytes, without a significant effect on osteoclasts. In one embodiment, the bisphosphonate is not 1-amino-3-(N,N-dimethylamino)-propyliden-1, 1-bisphosphonic acid or its pharmaceutically acceptable salt. An increase in osteoblast life span can lead to an increase in bone mass, i.e., an anabolic effect. Preservation of osteocyte life span can increase bone strength, which may be disproportional to the increase in bone mass.

The invention is based on the fundamental discovery that selected bisphosphonates increase bone strength by inhibiting osteocyte and osteoblast apoptosis without substantially affecting osteoclast activity, and thus resorption. In one embodiment, a lack of significant resorption is defined as minimal effect on bone resorption, for example, an effect of decreasing bone resorption by less than 10%, preferably less than 5%, and more preferably less than 2% versus an appropriate control. Lack of significant resorption can be assessed in vitro using the fetal murine long bone assay, or in vivo in ovariectemized mice or postmenopausal women using BMD or biochemical resorption markers (Brown et al., *J. Bone Miner. Res.* 1998, 13:253–258; van Beek E et al., *J. Bone Miner. Res.* 1996, 11:1492–1497). In one embodiment, the compound is one other than than 1-amino-3-N,N-dimethylamino)propyliden-1,1-bisphosphonic acid (IG9402), or its pharmaceutically acceptable salt.

Decreased osteoclast activity is associated with decreased remodeling (resorption), which may decrease the quality of bone over time. It was previously thought that the decreased activity of osteoclasts was essential for the activity of bisphosphonates, based on an antiresorption mechanism. This led to the conclusion that bisphosphonates acted as antiresorptives, with possible side effect of decreased bone quality over time. WO 97/02827 disclosed for the first time a bisphosphonate (IG9402) which acts as an anabolic agent without antiresorptive properties. WO 97/02827 did not describe how IG9402 acts as a treatment for osteoporosis without affecting resorption, and therefore, one could not effectively select or design new compounds with these desired properties. This invention presents the fundamental discovery that one essential action of bisphosphonates is the inhibition of apoptosis of osteoblasts and osteocytes, and that the antiresoptive activity (i.e., osteoclast activity) can be decoupled from the apoptosis of osteoblasts and osteocytes. Given this information, one of ordinary skill can select or design a new bisphosphonate which provides these properties as a superior agent to increase bone strength, simply by screening candidate bisphosphonates using identified bone cell assays as described herein or other known methods.

It has also been discovered that the rapid (i.e., within five minutes) activation of ERKs (extracellular signal regulated kinases), which is involved in the inhibition of apoptosis of osteoblasts and osteocytes, can be decoupled from the effect of selected bisphosphonates on osteoclasts and remodeling. Therefore, in another embodiment, a method is presented for treating a host in need of increasing bone strength, that includes selecting or designing a bisphosphonate which causes a rapid activation of ERK in osteoblasts or osteocytes without a significant effect on osteoclasts.

In yet another embodiment of the present invention, there is provided a method of screening for a compound that increases bone strength, that includes the steps of:

1. a) contacting osteocytes with a test compound; b) comparing the number of apoptotic osteocytes treated with the test compound with the number of apoptotic osteocytes not treated with the test compound; and c) determining the effect of the test compound on apoptosis of osteocytes;

2. contacting osteoblasts with the test compound; b) comparing the number of apoptotic osteoblasts treated with the test compound with the number of apoptotic osteoblasts not treated with the test compound; and c) determining the effect of the test compound on apoptosis of osteoblasts; and also 3. contacting osteoclasts with the test compound; b) comparing the number of apoptotic osteoclasts treated with the test compound with the number of apoptotic osteoclasts not treated with the test compound; and c) determining the effect of the test compound on apoptosis of osteoclasts.

In one embodiment, a bisphosphonate which falls within the scope of the present invention is one that causes a significant antiapoptotic effect on osteoblasts and osteocytes (for example, at an in vivo dosage of at least 0.1 ng/kg body weight) or in vitro (at least 10% more apoptotic cells than untreated cells, and preferably, 20, 50 or 75% more apoptotic cells than untreated cells), yet does not have a significant effect on osteoclasts (i.e., less than 10% increase in apoptotic osteoclastic cells, and preferably, less than 5 or 2% apoptotic cells). In another embodiment, the test compound induces the phosphorylation of extracellular signal regulated kinase (ERK) (for example, when administered in vivo at a dosage of at least 0.1 ng/kg body weight) or in vitro in osteoblastic or osteocytic cells.

In another embodiment of the present invention, there is provided a method of screening for a compound that prevents glucocorticoid-induced apoptosis of osteocytes without significant bone resorption, comprising the steps of: a) treating osteocytes with a test compound, thereby producing treated osteocytes; b) contacting the treated osteocytes with a glucocorticoid; c) comparing the number of osteocytes undergoing apoptosis in the glucocorticoid-treated osteocytes pretreated with the test compound with the number of osteocytes undergoing apoptosis in the glucocorticoid-treated osteocytes not pretreated with the test compound; and d) determining the effect of the test compound on bone resorption. A lower number of osteocytes undergoing apoptosis in the glucocorticoid-treated osteocytes pretreated with the test compound than the number of osteocytes undergoing apoptosis in the glucocorticoid-treated osteocytes not pretreated with the test compound indicates a test compound that prevents glucocorticoid-induced apoptosis of osteocytes. A compound should be selected that does not have a signficant effect. on bone resorption. Lack of significant resorption can be assessed in vitro using the fetal murine long bone assay, or in vivo in ovariectomized mice or postmenopausal women using BMD or biochemical resorption markers (Brown et al., *J. Bone Miner. Res.* 1998, 13:253–258; van Beek E et al., *J. Bone Miner. Res.* 1996, 11:1492–1497).

Evidence is presented herein that bisphosphonates and calcitonin act directly on osteocytes to inhibit apoptosis induced by glucocorticoids or other pro-apoptotic signals. The effect of these agents can be reproduced in osteoblastic cells as well. Significantly, the anti-apoptotic effect of bisphosphonates occurs with doses 100–1000 times lower than those at which these agents inhibit osteoclast resorption. This phenomenon is also demonstrated for bisphosphonates that do not have antiresorptive properties (e.g., IG-9402).

In yet another embodiment of the present invention, there is provided a method of decreasing bone fragility in an individual in need of such treatment, comprising the step of: a) administering to said individual an effective amount of a pharmaceutical composition comprising an aminobisphosphonate, or salts or hydrates thereof, wherein said administration reduces the number of osteocytes and osteoblasts undergoing apoptosis without significant bone resorption, thereby decreasing bone fragility in said individual.

The present invention indicates that at least part of the anti-fracture efficacy of the bisphosphonate agents for the treatment of osteoporosis is due to the prevention of osteocyte apoptosis. Hence, the present invention discloses in vitro assays of osteocyte and osteoblast apoptosis using osteocytic cell lines that can be used for screening bisphosphonate or calcitonin compounds analogs or other novel agents with anti-fracture properties, thus allowing for the discovery of useful new drugs. The anti-apoptotic efficacy of promising compounds can be subsequently verified in whole animals and human biopsies with techniques which have already been developed for this purpose and have been shown to perform reliably (Weinstein et al., *J. Clin. Invest.*, 102:274–282, 1998).

In the present invention, certain bisphosphonates are used, which, by means of changes in their chemical structure, have reduced anti-osteoclast action. The present invention describes bisphosphonate compound that are capable of reducing the process of osteocytic apoptosis at doses which fail to affect the osteoclast, apparently by a different mechanism of action from which some of the known bisphosphonates act, such that an "osteocyte-selective" method of treatment is disclosed herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A is a bar graph demonstrating the induction of apoptosis in osteocytes by treatment with etoposide, TNF-α, or dexamethasone. Cells were incubated for 1 h in DEVO-CHO, and subsequently incubated for an additional 6 h in the presence of 50 μM etoposide, 1 nM TNF-α, or $10^{-6}$ M dexamethasone. The degree of apoptosis is expressed as a percentage of dead cells as determined by trypan blue uptake. Bars represent the mean ±S.D. of three independent measurements. Data were analyzed by one-way ANOVA. * indicates P<0.05 versus control (Student-Newman-Keuls method). FIG. 1B is a fluorescent micrograph demonstrating characteristic features of osteocyte apoptosis including chromatin condensation and nuclear fragmentation. Osteocytes stably transfected with nuclear green fluorescent protein were maintained in for 6 h in the presence of vehicle, 50 μM etoposide, 1 nM TNF-α, or $10^{-6}$ M dexamethasone. Cells were visualized at 400×.

FIG. 6A is a an autoradiograph of MLO-Y4 cells stimulated with $10^{-7}$ M alendronate (A) or IG-9402 (IG) for the indicated times. Phosphorylated ERK1/2 and total ERK1/2 were determined by Western blot analysis as described in Methods and Materials. FIG. 6B is series of bar graph plots showing Phospho-ERK/ERK ratios over time. Ratios were obtained by quantifying the intensity of the bands in the autoradiograms using a scanner.

FIG. 7 contains a series of bar graph plots and an autoradiograph illustrating that the anti-apoptotic effect of bisphosphonates involves ERK activation.

In FIG. 9A MLO-Y4 cells were stimulated with 5 ng/ml of sCT for the indicated times. Phosphorylated ERK1/2 and total ERK1/2 were determined by Western blot analysis as described in Methods. In FIG. 9B cells were treated for 30 min with PD98059 or with UO126, followed by addition of 5 ng/ml of sCT. After 1 hour, $10^{-6}$ M dexamethasone was added and cultures incubated for 6 hours. The percentage of apoptotic cells was determined by trypan blue exclusion, as in FIG. 1A. Bars represent the mean ±S.D. of three independent measurements. * indicates P<0.05 versus control by one-way ANOVA (Student-Newman-Keuls method).

DETAILED DESCRIPTION OF THE INVENTION

Figure 1A:
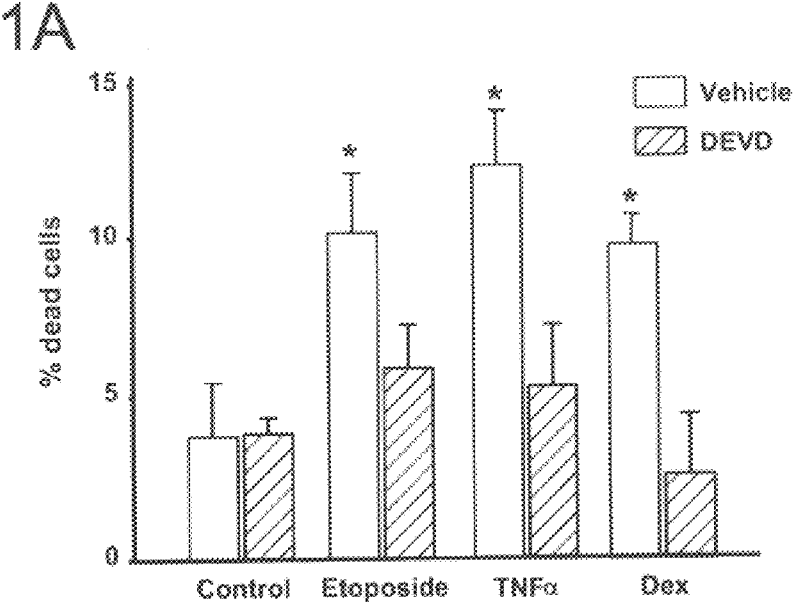
FIGS. 1A and 1B illustrate the induction of apoptosis in osteocytes.

The present invention is a method to increase bone strength in a manner that decreases fracture incidence, which may or may not include increasing bone mineral density ("BMD"). The invention includes administering an effective amount of a bisphosphonate to a host in need thereof to increase bone strength, which inhibits the apoptosis of osteoblasts and osteocytes, without a significant effect on osteoclasts. In one embodiment, the bisphosphonate is not 1-amino-3-(N,N-dimethylamino)-propyliden-1,1-bisphosphonic acid or its pharmaceutically acceptable salt. An increase in osteoblast life span can lead to an increase in bone mass, i.e., an anabolic effect. Preservation of osteocyte life span can increase bone strength, which may be disproportional to the increase in bone mass.

The invention is based on the fundamental discovery that selected bisphosphonates increase bone strength by inhibiting osteocyte and osteoblast apoptosis without substantially affecting osteoclast activity, and thus resorption. In one embodiment, a lack of significant resorption is defined as minimal effect on bone resorption, for example, an effect of decreasing bone resorption by less than 10%, preferably less than 5%, and more preferably less than 2% versus the control. Lack of significant resorption can be assessed in vitro using the fetal murine long bone assay, or in vivo in ovariectemized mice or postmenopausal women using BMD or biochemical resorption markers (Brown et al., *J. Bone Miner. Res.* 1998, 13:253–258; van Beek E et al., *J. Bone Miner. Res.* 1996, 11:1492–1497). In another embodiment, the compound is one other than than IG9402, or its salts or prodrugs, as disclosed in WO 97/02827.

Decreased osteoclast activity is associated with decreased remodeling (resorption), which may decrease the quality of bone over time. It was previously thought that the decreased activity of osteoclasts was essential for the activity of bisphosphonates, based on an antiresorption mechanism. This led to the conclusion that bisphosphonates acted as antiresorptives, with possible side effect of decreased bone quality over time. This invention presents the fundamental discovery that one essential action of bisphosphonates is the inhibition of apoptosis of osteoblasts and osteocytes, and that the antiresoptive activity can be decoupled from the apoptosis of osteoblasts and osteocytes.

It has also been discovered that the rapid activation of ERKs (extracellular signal regulated kinases), which is involved in the apoptosis of osteoblasts and osteocytes, can be decoupled from the effect of selected bisphosphonates on osteoclasts and remodeling.

In an embodiment of the present invention, there is provided a method of screening for a compound that prevents apoptosis of osteocytes without significant bone resorption, comprising the steps of: a) contacting osteocytes with a test compound; b) comparing the number of apoptotic osteocytes treated with the test compound with the number of apoptotic osteocytes not treated with the test compound; and c) determining the effect of the test compound on bone resporption. A lower number of apoptotic osteocytes treated with the test compound than apoptotic osteocytes not treated with the test compound indicates that the test compound prevents apoptosis of osteocytes. A compound should be selected that does not have a signficant effect on bone resorption.

In another embodiment of the present invention, there is provided a method of screening for a compound that prevents glucocorticoid-induced apoptosis of osteocytes without significant bone resorption, comprising the steps of: a) treating osteocytes with a test compound, thereby producing treated osteocytes; b) contacting the treated osteocytes with a glucocorticoid; c) comparing the number of osteocytes undergoing apoptosis in the glucocorticoid-treated osteocytes pretreated with the test compound with the number of osteocytes undergoing apoptosis in the glucocorticoid-treated osteocytes not pretreated with the test compound; and d) determining the effect of the test compound on bone resorption. A lower number of osteocytes undergoing apoptosis in the glucocorticoid-treated osteocytes pretrleated with the test compound than the number of osteocytes undergoing apoptosis in the glucocorticoid-treated osteocytes not pretreated with the test compound indicates a test compound that prevents glucocorticoid-induced apoptosis of osteocytes. A compound should be selected that does not have a signficant effect on bone resorption. Lack of significant bone resorption can be assessed in vitro using the fetal murine long bone assay, or in vivo in ovariectomized mice or postmenopausal women using BMD or biochemical resorption markers (Brown et al., *J. Bone Miner. Res.* 1998, 13:253–258; van Beek E et al., *J. Bone Miner. Res.* 1996, 11:1492–1497).

In yet another embodiment of the present invention, there is provided a method of screening for a compound that increases bone strength, that includes the steps of:

1. a) contacting osteocytes with a test compound; b) comparing the number of apoptotic osteocytes treated with the test compound with the number of apoptotic osteocytes not treated with the test compound; and c) determining the effect of the test compound on apoptosis of osteocytes;
2. contacting osteoblasts with the test compound; b) comparing the number of apoptotic osteoblasts treated with the test compound with the number of apoptotic osteoblasts not treated with the test compound; and c) determining the effect of the test compound on apoptosis of osteoblasts; and also
3. contacting osteoclasts with the test compound; b) comparing the number of apoptotic osteoclasts treated with the test compound with the number of apoptotic osteoclasts not treated with the test compound; and c) determining the effect of the test compound on apoptosis of osteoclasts.

In one embodiment, a bisphosphonate which falls within the scope of the present invention is one that causes a significant antiapoptotic effect on osteoblasts and osteocytes (for example, at an in vivo dosage of at least 0.1 ng/kg body weight) or in vitro (at least 10% more apoptotic cells than untreated cells, and preferably, at least 20, 50 or 75% more apoptotic cells than untreated cells), yet does not have a significant effect on osteoclasts (i.e., less than 10% increase in apoptotic osteoclastic cells, and preferably, less than 5 or 2% apoptotic cells). In another embodiment, the test compound induces the phosphorylation of extracellular signal regulated kinase (ERK) (for example, when administered in vivo at a dosage of at least 0.1 ng/kg body weight) or in vitro in osteoblastic or osteocytic cells, without significant effect on osteoclast cells.

Evidence is presented herein that bisphosphonates and calcitonin act directly on osteocytes to inhibit apoptosis induced by glucocorticoids or other pro-apoptotic signals. The effect of these agents can be reproduced in osteoblastic cells as well. Significantly, the anti-apoptotic effect of bisphosphonates sometimes occur with doses 100–1000 times lower than those at which these agents inhibit osteoclast resorption. Importantly, this phenomenon can occur Using selected bisphosphonates that do not have antiresorptive properties. IG-9402 is the prototype example of a compound that has these properties, and others can be identified given the disclosure herein.

In yet another embodiment of the present invention, there is provided a method of decreasing bone fragility in an individual in need of such treatment, comprising the step of administering to said individual an effective amount of a pharmaceutical composition comprising an aminobisphosphonate (i.e., a bisphosphonate that has a substituent amino group) other than IG9402, or salts or hydrates thereof, wherein said administration reduces the number of osteocytes and osteoblasts undergoing apoptosis without significant bone resorption, thereby decreasing bone fragility in said individual.

The present invention indicates that at least part of the anti-fracture efficacy of the selected bisphosphonate agents for the treatment of osteoporosis is due to the prevention of osteocyte apoptosis. Hence, the present invention discloses in vitro assays of osteocyte and osteoblast apoptosis using osteocytic cell lines that can be used for screening bisphosphonate, calcitonin or estrogenic compounds analogs or other novel agents with anti-fracture properties, thus allowing for the discovery of useful new drugs. The antiapoptotic efficacy of promising compounds can be subsequently verified in whole animals and human biopsies with techniques which have already been developed for this purpose and have been shown to perform reliably (Weinstein et al., *J. Clin. Invest.*, 102:274).

In the present invention, certain bisphosphonates are used, which, by means of changes in their chemical structure, have reduced anti-osteoclast action. The present invention describes bisphosphonate compounds that are capable of reducing the process of osteocytic apoptosis at doses which fail to affect the osteoclast, apparently by a different mechanism of action from which some of the known bisphosphonates act, such that an "osteocyte-selective" method of treatment is disclosed herein.

I. Definitions

The term "bone mass" refers to the mass of bone mineral and is typically determined by Dual-Energy X-Ray Absorbtiometry (DEXA).

The term "bone strength" refers to resistance to mechanical forces and can be measured by any known method, including vertebrae compression strength or three point-bending of long bones.

The term "bone quality" refers to normal collagen orientation without excessive accumulation of unmineralized bone matrix, and can be measured by any known method, including undecalcified bone histomorphometry.

The term "bone anti-resorption agent" refers to a compound that blocks bone resorption by suppressing remodeling or the activity and/or lifespan of osteoclasts.

The term "osteopenia" refers to decreased bone mass below a threshold which compromises structural integrity.

As used herein, the terms "metabolic bone disease", "orthopedic bone disease" or "dental disease" are defined as conditions characterized by decreased bone mass and/or structural deterioration of the skeleton and/or teeth.

As used herein, the term "apoptosis" refers to programmed cell death characterized by nuclear fragmentation and cell shrinkage and morphological criteria as detected by techniques including but not limited to: DNA end-labeling, DNA fragmentation analysis, and immunohistochemical analysis.

As used herein, the terms "glucocorticoid" and "glucocorticoid analog" are defined as substances that bind to the glucocorticoid receptor.

The term "host", as used herein, refers to any bone-containing animal, including, but not limited to humans, other mammals, canines, equines, felines, bovines (including chickens, turkeys, and other meat producing birds), cows, and bulls.

The term "bisphosphonate" as used here in refers to a compound that has two or more phosphonate groups.

II. Compounds Useful in the Invention.

The essential aspect of this invention is the discovery that one can decouple the osteocyte and osteoblast activity in bone disease and repair. While it had been previously published that IG9402 can be used to treat bone disease without antiresportive activity, the mechanism for how that worked was elusive. The mechanism is now understood, which provides a basis for the intelligent selection of bisphosphonates with these limited selective and improved properties. Therefore, in one embodiment, the invention is the use of a bisphosphonate compound other than IG9402 to increase bone strength which does not have significant antiresorptive properties, as determined by a lack of effect on osteoclasts.

A lack of significant resorption is defined as minimal effect on bone resorption, for example, an effect of decreasing bone resorption by less than 10%, preferably less than 5%, and more preferably less than 2% versus the control. Lack of significant resorption can be assessed in vitro using the fetal murine long bone assay, or in vivo in ovariectemized mice or postmenopausal women using BMD or biochemical resorption markers (Brown et al., *J. Bone Miner. Res.* 1998, 13:253–258; van Beek E et al., *J. Bone Miner. Res.* 1996, 11:1492–1497). In another embodiment, the compound is one other than than IG9402, or its salts or prodrugs, as disclosed in WO 97/02827.

The selected bisphosphonate should also cause the rapid activation of extracellular regulated kinases, determined by any appropriate assay, including that described below.

III. Methods for Using the Active Compounds

The active bisphosphonate compounds which satisfy the criteria set out in detail herein can be used to treat a wide variety of medical conditions, including any condition in which it is helpful or necessary to build bone mass and decrease bone fragility. Because of the discovery of the fundamental basis for bone loss and fragility (inappropriate osteoblastic and osteocytic apoptosis), one can for the first time envision the building of healthy bone as opposed to merely treating bone loss.

The active compounds can be used as bone anabolic agents in a host, including a human, to strengthen bone for strenuous physical activities such as sports or manual labor, and to strengthen bone in persons or other hosts who do not have osteoporosis but might be subject to osteoporosis in the future because the host is in a risk group for that disease. Other uses for a bone anabolic agent in humans include the treatment of hosts, including persons who are born with naturally thin, small, or unusually fragile bones, including weak teeth, persons who have a genetic predisposition to a bone catabolic disease, or an orthopedic bone disease such as joint degeneration, non-union fractures, orthopedic problems caused by diabetes, periimplantitis, poor responses to bone grafts, implants, or fracture.

These compounds can be used to increase the bone mass and decrease bone fragility in horses and dogs used for labor as well as those used in sports such as racing. The compounds can also be used to increase the bone mass in chickens and turkeys used in meat production to increase the ease of processing.

Representative metabolic bone diseases are postmenopausal osteoporosis, senile osteoporosis in males and females, glucocorticoid-induced osteoporosis, immobilization-induced osteoporosis, weightlessness-induced osteoporosis (as in space flights), post-transplantation osteoporosis, migratory osteoporosis, idiopathic osteoporosis, juvenile osteoporosis, Paget's Disease, osteogenesis imperfecta, chronic hyperparathyroidism, hyperthyroidism, rheumatoid arthritis, Gorham-Stout disease, McCune-Albright syndrome and osteolytic metastases of various cancers or multiple myeloma. Characteristics of the orthopedic bone diseases are loss of bone mass, general bone fragility, joint degeneration, non-union fractures, orthopedic and dental problems caused by diabetes, periimplantitis, poor responses to bone grafts/implants/bone substitute materials, periodontal diseases, and skeletal aging and its consequences.

Compounds selected according to the present invention can also be used in disorders in which the classical antiresorptive property of bisphosphonates is not required, such as in the diagnosis, prophylaxis, and /or treatment of urolithiasis, ectopic calcifications, or as cytostatic drugs to the skeleton, either for diagnosis or for therapeutic purposes.

IV. Method for Screening for Compounds that Increase Bone Strength

The present invention includes a method of screening for a compound that prevents apoptosis of osteocytes, comprising the steps of: a) contacting osteocytes with a test compound; and b) comparing the number of apoptotic osteocytes treated with the test compound with the number of apoptotic osteocytes not treated with the test compound. A lower number of apoptotic osteocytes treated with the test compound than apoptotic osteocytes not treated with the test compound indicates a test compound that prevents apoptosis of osteocytes. The osteocytes may be contacted in vitro and in vivo. When contact is in vitro, the MLO-Y4 osteocytic or another appropriate cell line can be used. The test compound may be a bisphosphonate; more preferably an aminobisphosphnate. 3-(N,N-dimethylamino)-1-aminopropylyden-bisphosphonic acid (IG-9402), or salts or hydrates thereof is a prototype compound exhibiting such properties. Apoptosis of osteocytes is typically determined by fluorescent microscopy of MLO-Y4 cells stably transfected with nuclear green fluorescent protein or in stained cells, TUNEL, with Hoescht 33258 dye and video image analysis.

The present invention is also directed to a method of screening for a compound that prevents glucocorticoid-induced apoptosis of osteocytes, comprising the steps of: a) treating osteocytes with a test compound, thereby producing a group of treated osteocytes and a group of untreated osteocytes; b) contacting the treated osteocytes with a glucocorticoid; and c) comparing the number of osteocytes undergoing apoptosis in the glucocorticoid-treated osteocytes contacted with the test compound with the number of osteocytes undergoing alpoptosis in the glucocorticoid-treated osteocytes not contacted with the test compound. Generally, a lower number of osteocytes undergoing apoptosis in the glucocorticoid-treated osteocytes pre-treated with the test compound compared with the number of osteocytes undergoing apoptosis in the glucocorticoid-treated osteocytes not pre-treated with the test compound indicates that the test compound prevents glucocorticoid-induced apoptosis of osteocytes. Representative glucocorticoids include dexamethasone and prednisolone. Treatment and contact of the osteocytes may be either in vitro and in vivo. When the treatment and contact is in vitro, the osteocytes may be, for example, MLO-Y4 cells or MLO-Y4 cells stably transfected with green fluorescent protein. The test compound may be a bisphosphonate, and preferably an amino-bisphosphonate, or salts or hydrates thereof. Apoptosis of osteocytes is typically determined by a method selected from the group consisting of fluorescent microscopy of MLO-Y4 cells stably transfected with nuclear green fluorescent protein or in stained cells, TUNEL, with Hoescht 33258 dye and video image analysis. In yet another embodiment of the present invention, there is provided a method of screening for a compound that increases bone strength, that includes the steps of:

1. a) contacting osteocytes with a test compound; b) comparing the number of apoptotic osteocytes treated with the test compound with the number of apoptotic osteocytes not treated with the test compound; and c) determining the effect of the test compound on apoptosis of osteocytes;

2. contacting osteoblasts with the test compound; b) comparing the number of apoptotic osteoblasts treated with the test compound with the number of apoptotic osteoblasts not treated with the test compound; and c) determining the effect of the test compound on apoptosis of osteoblasts; and also 3. contacting osteoclasts with the test compound; b) comparing the number of apoptotic osteoclasts treated with the test compound with the number of apoptotic osteoclasts not treated with the test compound; and c) determining the effect of the test compound on apoptosis of osteoclasts.

In one embodiment, a bisphosphonate which falls within the scope of the present invention is one that causes a significant antiapoptotic effect on osteoblasts and osteoclasts (for example, at an in vivo dosage of at least 0.1 ng/kg body weight) or in vitro (at least 10% more apoptotic cells than untreated cells, and preferably, at least 20, 50 or 75% more apoptotic cells than untreated cells), yet does not have a significant effect on osteoclasts (i.e., less than 10% increase in apoptotic osteoclastic cells, and preferably, less than 5 or 2% apoptotic cells). In another embodiment, the test compound induces the phosphorylation of extracellular signal regulated kinase (ERK) (for example, when administered in vivo at a dosage of at least 0.1 ng/kg body weight) or in vitro in osteoblastic or osteocytic cells, without significant effect on osteoclast cells.

V. Method for Decreasing Bone Fragility

The present invention also provides a method of decreasing bone fragility in an individual in need of such treatment, comprising the step of administering to said individual an effective amount of a compound which (i) inhibits the apoptosis of osteocytes and/or osteoblasts (ii) without substantially affecting the activity of osteoclasts. In one embodiment, the compound is an amino-bisphosphonate, or salts or hydrates thereof other than IG 9402. This method may be useful in treating bone fragility such as bone fragility caused by treatment of the individual with glucocorticoids, treatment of the individual with compounds intended to increase bone mass, various forms of osteoporosis, and metabolic diseases of low bone mass and/or increased fragility. The pharmaceutical composition may further comprise an effective amount of a second agent for the purpose of producing a synergistic reaction between the second agent and the amino-bisphosphonate; the second agent is selected from the group consisting of calcium salts, fluorine salts, a bisphosphonate, vitamin D or a metabolite thereof such as calcitriol, estrogen, SERMS, anabolic hormones, or a precursor thereof and anabolic hormones.

The results presented herein represent the first demonstration of antiapoptotic effects of bisphosphonates and calcitonin on osteocytes, and are the first to indicate that in vitro screening for antiapoptotic effects on osteocytes can provide a means of selecting for compounds with superior anti-fracture efficacy from existing classes of therapeutic agents (i.e., bisphosphonates and calcitonin) or the means of identifying novel classes of compounds with anti-fracture efficacy (e.g., small molecules that will interfere with private apoptosis pathways).

The existing therapies for the treatment of conditions characterized by low bone mass have been developed based upon the assumption that such drugs influence only bone mineral density (BMD). Based upon the results disclosed herein, new kinds of therapeutic agents that preserve bone integrity may be developed based upon their ability to specifically inhibit osteocyte apoptosis without significantly affecting bone resorption. Such agents would be particularly useful in conditions in which osteocyte apoptosis is increased, such as in treatments with excess glucocorticoids or senile osteoporosis.

The present invention discloses prevention or treatment of those skeletal fragility conditions that attenuate, inhibit or shorten the useful life of the osteocyte and osteoblast, and in those conditions where osteoclast activity should not be disturbed. As examples, there may be cited senile fragility starting at menopause or andropause (natural osteopenia), fragility mediated by corticoids with or without osteopenia (steroid-dependent latrogenic fragility), fragility induced by antiosteoporotic agents or bone mass enhancers (e.g., fluorine, etidronate, clodronate) or fragility due to mechanostatic deadaptation.

Numerous non-amino-modified bisphosphonates, such as etidronate, clodronate, tiludronate, pamidronate, alendronate, risendronate, ibandronate and zolendronate, among others, have been applied in cyclical or continuous treatments in order to inhibit the osteoclasts, to decouple osteoclast-osteoblast activity and/or to promote the retention of mineralized structures. For example, in low doses, olpadronate has been shown to improve the material properties of calcified tissue (WO 96/1998 and derived patents, with priority Dec. 27, 1994). However, olpadronate is at the same time an effective inhibitor of the osteoclast and of bone resorption, and therefore, cannot be attributed to a selective effect on osteocytic activity (Roldan E J A et al., Drugs of the Future 1995, 20: 1123). Thus, the present invention is not related to the same.

In contrast, an amino-analog of olpadron ate, IG-9402, lacks such dual properties, which distinguishes it from known bisphosphonates (etidronate, clodronate, tiludronate, pamidronate, alendronate, risendronate, ibandronate, incadronate and zolendronate, among others) even when administered at concentrations 1000-fold higher than those previously described (van Beek E et al., *J. Bone Min. Res.* 1996, 11:1492). The preferred treatment consists of administering sufficient quantities of the selected bisphosphonates by oral or parenteral route. Therefore, on the basis of the potency ratio, the effective dose of IG-9402 in humans is estimated to be within the range of 0.01 to 1000 mg per application by oral route and 0.02 to 200 mg per application by parenteral route. IG-9402 (3-amino-1 aminopropylyden-bisphosphonic acid) and its salts and hydrates is a prototype of the selected compound. The potency ratio of IG-9402 to affect the osteoclast is ⅙ that of pamidronate (van Beek E et al., *J. Bone Min. Res.* 1996, 11:1492), so that the optimal quantities to be used for the treatments described herein are within the range of 12.5 to 75 mg per application by oral route and 2.5 to 15 mg per application by intravenous infusion. Oral administration formulations are preferable given the mild intervention in bone metabolism exerted by this route. However, injectable treatments may provide useful alternatives. Liquid oral formulations are preferred, especially when the bisphosphonate is dissolved inside a soft capsule. Formulations with a gastroresistant coating are preferred to avoid exposure of the sensitive mucosa of the esophagus and stomach to the bisphosphonate. See *Remington's Pharmaceutical Science*, 17th Ed. (1990) Mark Publishing Co., Easton, Pa.; and *Goodman and Gilman's: The Pharmacological Basis of Therapeutics* 8th Ed (1990) Pergamon Press.

VI. Combination Therapy

In one aspect of the invention, one of the active compounds described herein can be administered to a host to increase bone mass in combination with a second pharmaceutical agent. The second pharmaceutical agent can be a bone antiresorption agent, a second bone mass anabolizing agent, an antioxidant, a dietary supplement, or any other agent that increases the beneficial effect of the active compound on bone structure, strength, density, or mass.

Any member of the ten classes of drugs described in the Background of the Invention that are used in the treatment of osteoporosis can be administered in combination with the primary active agent, including: an anabolic steroid, a bisphosphonate, a calcitonin, an estrogen or progesterone, a SERM such as raloxifene or tamoxifene, parathyroid hormone ("PTH") fluoride, Vitamin D or a derivative thereof, or a calcium preparations.

Nonlimiting examples of suitable agents for combination include, but are not limited to, alendronic acid, disodium clondronate, disodium etidronate, disodium medronate, disodium oxidronate, disodium pamidronate, neridronic acid, risedronic acid, teriparatide acetate, tiludronic acid, ipriflavone, potassium bicarbonate, progestogen, a thiazide, gallium nitrate, NSAIDS, plicamycin, aluminum hydroxide, calcium acetate, calcium carbonate, calcium, magnesium carbonate, and sucralfate.

Reducing agents, such as glutathione or other antioxidants may also be useful in combination with any of the compounds of the present invention. As used herein, the term antioxidant refers to a substance that prevents the oxidation of an oxidizable compound under physiological conditions. In one embodiment, a compound is considered an antioxidant for purposes of this disclosure if it reduces endogenous oxygen radicals in vitro. The antioxidant can be added to a cell extract under oxygenated conditions and the effect on an oxidizable compound evaluated. As nonlimiting examples, antioxidants scavenge oxygen, superoxide anions, hydrogen peroxide, superoxide radicals, lipooxide radicals, hydroxyl radicals, or bind to reactive metals to prevent oxidation damage to lipids, proteins, nucleic acids, etc. The term antioxidant includes, but is not limited to, the following classes of compounds: .

A) Dithiocarbamates

Dithiocarbamates have been extensively described in patents and in scientific literature. Dithiocarbamates and related compounds have been reviewed extensively for example, by G. D. Thorn et al. entitled "The Dithiocarbamates and Related Compounds," Elsevier, N.Y., 1962. Dithiocarboxylates are compounds of the structure A-SC(S)-B, which are members of the general class of compounds known as thiol antioxidants, and are alternatively referred to as carbodithiols or carbodithiolates. It appears that the -SC(S)-moiety is essential for therapeutic activity, and that A and B can be any group that does not adversely affect the efficacy or toxicity of the compound. A and B can be selected by one of ordinary skill in the art to impart desired characteristics to the compound, including size, charge, toxicity, and degree of stability, (including stability in an acidic environment such as the stomach, or basic environment such as the intestinal tract). The selection of A and B will also have an important effect on the tissue-distribution and pharmacokinetics of the compound. The compounds are preferably eliminated by renal excretion.

B) N-Acetyl Cysteine and its Derivatives

Cysteine is an amino acid with one chiral carbon atom. It exists as an L-enantiomer, a D-enantiomer, or a racemic mixture of the L- and D-enantiomers. The L-enantiomer is the naturally occurring configuration.

N-acetylcysteine (acetarnido-mercaptopropionic acid, NAC) is the Nacetylated derivative of cysteine. It also exists as an L-enantiomer, a D-enantiomer, an enantiomerically enriched composition of one of the enantiomers, or a racemic mixture of the L and D enantiomers. The term "enantiomerically enriched composition or compound" refers to a composition or compound that includes at least 95%, and preferably, at least 97% by weight of a single enantiomer of the compound. Any of these forms of NAC can be delivered as an antioxidant in the present invention. In one embodiment, a single isomer of a thioester or thioether of NAC or its salt, and most preferably, the naturally occurring L-enantiomer, is used in the treatment process.

N-acetylcysteine exhibits antioxidant activity (Smilkstein, Knapp, Kulig and Rumack, *N. Engl. J. Med.* 1988, Vol. 319, pp. 1557–62; Knight, K. R., MacPhadyen, K., Lepore, D. A., Kuwata, N., Eadie, P. A., O'Brien, B. *Clinical Sci.*, 1991, Vol. 81, pp. 31–36; Ellis, E. F., Dodson, L. Y., Police, R. J., *J. Neurosurg.*, 1991, Vol. 75, pp. 774–779). The sulfhydryl functional group is a well characterized, highly reactive free radical scavenger. N-acetylcysteine is known to promote the formation of glutathione (a tri-peptide, also known as g-glutamylcysteinylglycine), which is important in maintaining cellular constituents in the reduced state (Berggren, M., Dawson, J., Moldeus, P. *FEBS Lett.*, 1984, Vol. 176, pp. 189–192). The formation of glutathione may enhance the activity of glutathione peroxidase, an enzyme which inactivates hydrogen peroxide, a known precursor to hydroxyl radicals (Lalitha, T., Kerem, D., Yanni, S., *Pharmacology and Toxicology*, 1990, Vol. 66, pp. 56–61)

N-acetylcysteine exhibits low toxicity in vivo, and is significantly less toxic than deprenyl (for example, the $LD_{50}$ in rats has been measured at 1140 and 81 mg/kg intravenously, for N-acetylcysteine and deprenyl, respectively).

N-acetyl cysteine and derivatives thereof are described, for example, in WO/95/26719. Any of the derivatives described in this publication can be used in accordance with this invention.

C) Scavengers of Peroxides, including but not limited to catalase and pyruvate.

D) Thiols including dithiothreitol and 2-mercaptoethanol.

E) Antioxidants which are inhibitors of lipid peroxidation, including but not limited to Trolox™, BHA, BHT, aminosteroid antioxidants, tocopherol and its analogs, and lazaroids.

F) Dietary antioxidants, including antioxidant vitamins (vitamin C or E or synthetic or natural prodrugs or analogs thereof), either alone or in combination with each other, flavanoids, phenolic compounds, caratenoids, and alpha lipoic acid.

G) Inhibitors of lipoxygenases and cyclooxygenases, including but not limited to nonsteriodal antiinflammatory drugs, COX-2 inhibitors, aspirin-based compounds, and quercetin.

H) Antioxidants manufactured by the body, including but not limited to ubiquinols and thiol antioxidants, such as, and including glutathione, Se, and lipoic acid.

I) Synthetic Phenolic Antioxidants: inducers of Phase I and II drug-metabolizing enzymes.

VII. Pharmaceutical Compositions

An active compound or its pharmaceutically acceptable salt, selected according to the criteria described in detail herein, can be administered in an effective amount to treat any of the conditions described herein, optionally in a pharmaceutically acceptable carrier or diluent.

The active materials can be administered by any appropriate route for systemic, local or topical delivery, for example, orally, parenterally, intravenously, intradermally, subcutaneously, buccal, intranasal, inhalation, vaginal, rectal or topically, in liquid or solid form. Methods of administering the compound of the invention may be by specific dose or by controlled release vehicles.

A preferred mode of administration of the active compound is oral. Oral compositions will generally include an inert diluent or an edible carrier. The active compound can be enclosed in gelatin capsules or compressed into tablets. For the purpose of oral therapeutic administration, the compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; and/or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as an estrogen like 17β-estradiol or ethinyl estradiol; an estrogen or androgen with insubstantial transcriptional activity, as described in **; bisphosphonates like alendronate, etidronate, pamidronate, risedronate, tiludronate, zoledronate, cimadronate, clodronate, ibandronate, olpadronate, neridronate, EB-1053; calcitonin of salmon, eel or human origin; and anti-oxidants like glutathione, ascorbic acid or sodium bisulfite. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; chelating agents such as ethylenediaminetetraacetic acid (EDTA); buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted with monoclonal antibodies to surface antigens of specific cells) are also pharmaceutically acceptable carriers. These may be prepared according to, methods known to those skilled in the art, for example, as described in U.S. Pat. No. 4,5221,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and/or cholesterol) in an inorganic solvent that is then evaporated, leaving behind a thin film of dried lipid on the surface of the container. An aqueous solution of the active compound or its monophosphate, diphosphate, and/or triphosphate derivative (s) is then introduced into the container. The container is then swirled by hand to free lipid material from the sides of the container and to disperse lipid aggregates, thereby forming the liposomal suspension.

The dose and dosage regimen will depend upon the nature of the metabolic bone disease, the characteristics of the particular active compound, e.g., its therapeutic index, the patient, the patient's history and other factors. The amount of an activator of non-genomic estrogen-like signaling compound administered will typically be in the range of about 1 pg/kg to about 10 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and Goodman and Gilman's: The Pharmacological Basis of Therapeutics 8th Ed (1990) Pergamon Press.

For parenteral administration, the active compound will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. An activator of non-genomic estrogen-like signaling compound will typically be formulated in such vehicles at concentrations of about 10 pg/ml to about 10 mg/ml.

The concentration of the compound in the drug composition will depend on absorption, inactivation, and excretion rates of the drug as well as other factors known to those of skill in the art. It is to be noted that dosage values will also vary with the severity of the condition to be alleviated. Additionally, the active ingredient may be administered at once, or may be divided into a number of smaller doses to be administered at varying intervals of time. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

VIII. Methods and Materials

The data presented herein in were achieved utilizing the following materials and methods.

A. Materials

The bisphosphonates used in this study were provided by Gador S. A. (Buenos Aires, Argentina). Bovine calf serum was purchased from Hyclone (Logan, Utah). Fetal bovine serum (FBS) was purchased from Summit (Collins, Colo.). Recombinant murine TNF-α was obtained from Genzyme (Cambridge, Mass.). Phenol red-free αMEM and trypsin-EDTA were purchased from Gibco BRL (Gaithersburg, Md.). Etoposide, geneticin (G418), and calf skin collagen type I were obtained from Sigma Chemical Co (St. Louis, Mo.). Collagenase type 2 was purchased from Worthington Biochemical Corporation (Freehold, N.J.). PD98059 was purchased from New England Biolabs (Beverly, Mass.). U0126 was provided by Dr. J. M. Trzaskos (DuPont Merck Research Laboratories, Wilmington, Del.). The caspase-3 inhibitor Asp-Glu-Val-Asp-aldehide (DEVD-CHO) was purchase from Biomol Research Lab., Inc. (Plymouth Meeting, Pa.). DEVD conjugated with 7-amino-4-trifluoromethyl coumarin (DEVD-AFC) was from Biorad (Hercules, Calif.). The mouse monoclonal antibody anti phospho-ERK1/2, the rabbit polyclonal antibody anti phosphorylated and unphosphorylated ERK1/2 and secondary antimouse or antirabbit antibodies conjugated with HRP were purchased from Santa Cruz Biotechnology (Santa Cruz, Calif.). Salmon calcitonin (sCT) was purchased from Bachem (Torrance, Calif.). $^{125}I$ was obtained from Amersham (Arlington Heights, Ill.).

B. Methods

Cell Culture

The murine long bone-derived osteocytic cell line MLO-Y4 was provided by Dr. Lynda Bonewald (University of Texas Health Center at San Antonio, Tex.). Cells were cultured in phenol red-free αMEM supplemented with 5% FBS, 5% bovine calf serum, 100 U/ml penicillin and 100 µg/ml streptomycin. Cells were plated at $1-2 \times 10^4$ cells/cm$^2$ on collagen type I coated plates, as described previously (Kato, et al., 1997. *J. Bone Miner. Res.* 12:2014–2023). Murine calvaria cells were obtained from neonatal (3- to 6-day old) C57BL/6J mice by controlled digestion with collagenase, as previously described (Bellido, et al., 1997. *Endocrinology* 138:3666–3676). After isolation, cells were cultured in 10% FBS at $1-2 \times 10^4$ cells/cm$^2$ until 90–95% confluence. Subsequently, cells were harvested and frozen for later use. UMR-106-06 cells were cultured in phenol red-free MEM supplemented with 10% FBS, 1% non-essential aminoacids, 100 U/ml penicillin, and 100 µg/ml streptomycin (Sakagami, et al., Manolagas. 1993. *J. Bone Miner. Res.* 8:811–816).

Trypan Blue Uptake

Nonadherent cells were combined with adherent cells released from the culture dish using trypsin-EDTA, resuspended in medium containing serum, and collected by centrifugation. Subsequently, 0.04% trypan blue was added and the percentage of cells exhibiting both nuclear and cytoplasmic staining was determined using a hemocytometer. At least 100 cells per condition were counted.

Establishment of MLO-Y4 Cells Stable Transduced with Green Fluorescent Protein

The retroviral vector containing the nuclear green fluorescent protein (GFP) was provided by Dr. Charles O'Brien (University of Arkansas for Medical Sciences, Little Rock, Ark.). The SV40 large T antigen nuclear localization sequence was attached to the carboxyterminus of the cDNA construct encoding GFP and subcloned into the pLXSN retroviral vector (CLONTECH, Palo Alto, Calif.). The plasmid harboring the retroviral construct was transiently transfected into the packaging cell line Phoenix Eco using SuperFect (Qiagen, Santa Clarita, Calif.). Supernatants containing retroviral particles were collected 24–48 h after transfection, and used immediately to infect cell cultures. Subconfluent MLO-Y4 osteocytic cells were exposed to viral supernatants in the presence of 8 µg/ml polybrene for 8 h and then incubated in fresh culture medium for 16 h. Subsequently, cells were exposed to the supernatants containing the viral particles once more before being trypsinized and plated at low density. Transduced cells were selected by culturing them in the presence of 400 µg/ml of G418 for three weeks.

Quantification of Apoptotic Cells

MLO-Y4 osteocytic cells and calvaria osteoblastic cells were treated for 1 hour in the absence or presence of different BPs or sCT. Subsequently, dexamethasone, etoposide or TNF-α were added to obtain final concentrations of $10^{-6}$ M, 50 µM, or 1 nM, respectively, and cells were incubated for additional 6 h. The effect of PD98059 (50 $\mu$M) or UO126 (1 $\mu$M) was evaluated by pretreating the cells with the inhibitors for 30 min before adding the BPs or sCT. In the experiment using the membrane permeable caspase inhibitor DEVD, cells were cultured for 1 hour with 50 nM DEVD-CHO and subsequently the pro-apoptotic agents were added to reach the final concentrations indicated above. MLO-Y4 cells stable transduced with nuclear GFP were fixed in neutral buffer formalin for 8 min, and apoptosis was assessed by enumerating cells exhibiting chromatin condensation and nuclear fragmentation under a fluorescent microscope. At least 500 cells from fields selected by systematic random sampling were examined for each experimental condition. For the detection of apoptotic cells using the TUNEL reaction (transferase-mediated biotin-dUTP nick end-labeling) with Klenow terminal deoxynucleotidyl transferase (Oncogene Research Products, Cambridge, Mass.), MLO-Y4 cells were cultured with either vehicle or $10^{-7}$M alendronate for 1 hour and subsequently dexamethasone was added to reach $10^{-6}$ M. After 6 hours, cells were fixed in neutral buffer formalin for 10 min followed by 80% ethanol for 1 hour. The TUNEL reaction was performed according to the manufacturer's instructions, using 0.15% $CuSO_4$ for color enhancement. Negative controls were made by omitting the transferase from the reaction. Cells presenting brown nuclear staining were considered positive. More than 500 cells per condition were analyzed. Apoptosis of parental MLO-Y4 or calvaria cells was quantified by trypan blue staining (Jilka, et al., 1998. *J. Bone Miner. Res.* 13:793–802). Nonadherent cells were combined with adherent cells released from the culture dish using trypsin-EDTA, resuspended in medium containing serum, and collected by centrifugation. Subsequently, 0.04% trypan blue was added and the percentage of cells exhibiting both nuclear and cytoplasmic staining was determined using a hemocytometer. At least 100 cells per condition were counted.

Caspase-3 Activity

Caspase-3 activity was measured by determining the degradation of the fluorometric substrate DEVD, that contains acid sequence of the caspase-3 cleavage site in poly (ADP-ribose)polymerase (PARP) (Schlegel, et al., 1996. *J. Biol. Chem.* 271:1841–1844) conjugated with 7-amino-4-trifluoromethyl coumarin (DEVD-AFC). Cells were lysed in 20 mM Tris-HCl (H 7.5), 150 mM NaCl, 1 mM EDTA, 10 mM NaF, 1 mM sodium orthovanadate, 5 $\mu$g/ml leupeptin, 0.14 U/ml aprotinin, 1 mM phenylmethylsulfonylfluoride, and 1% Triton X-100. Protein concentration was measured using a Bio-Rad detergent compatible kit (Hercules, Calif.). Lysates (100 $\mu$g protein) were incubated with 50 $\mu$M DEVD-AFC in 50 mM HEPES, pH 7.4, 100 mM NaCl, 0.1% CHAPS, 10 mM DTT, 1 mM EDTA, 10% glycerol, in the absence or presence of the irreversible inhibitor DEVD-CHO for 60 min. The released fluorescent AFC was measured in a microplate fluorescence reader FL500 (Bio Tek Instruments, Winooski, Vt.) with excitation/emission wavelengths of 340/542 nm.

Western Blot Analysis

Semiconfluent (75–80%) MLO-Y4 cells were incubated in medium without serum (in the absence or presence of 50 $\mu$M PD98059 or 1 $\mu$M UO126) for 25 min, and treated with $10^{-7}$ M alendronate, IG-9402 or etidronate for the last 0.5, 1, 2, 5, 10 or 15 min, or with 5 ng/ml sCT for the last 2, 5, 10, or 15 min. Monolayers were washed with cold 20 mM Tris-HCl (pH 7.5), 150 mM NaCl, 1 mM sodium orthovanadate and lysed in the lysis buffer mentioned above. Insoluble material was pelleted in a microcentrifuge at 14,000×rpm for 10 mn. The phosphorylation status of ERK1/2 was analyzed by immunoblotting, as previously described (Bellido, et al., 1997. *Endocrinology* 138:3666–3676). Proteins (10 $\mu$g) were separated on 7.5% SDS-polyacrylamide gels and electrotransferred to a polyvinylidene difluoride membrane. Immunoblotting was performed using a mouse monoclonal antibody recognizing tyrosine phosphorylated ERK1/2, or a rabbit polyclonal antibody recognizing total ERK1/2, followed by incubation with either an antimouse or an antirabbit antibody conjugated with horseradish peroxidase. Blots were developed using Chemiluminescence according to the manufacturer's recommendations. Quantitation of the intensity of the bands in the autoradiograms was performed using a scanner (Microtek Lab., Redondo Beach, Calif.).

Calcitonin Binding Assay sCT was labeled with $^{125}$I in the presence of chloramine T using a standard protocol. Binding of $^{125}$I-sCT to MLO-Y4 or UMR-106-06 cells was performed using a whole cell assay. Cells were harvested by trypsinization, washed twice with PBS, resuspended in culture medium without serum, and incubated in triplicates (1.25×10$^5$/tube) with $10^{-8}$ M [$^{125}$I]sCT in the absence or presence of 100-fold molar excess of unlabeled sCT, for 1 h at room temperature. Subsequently, cells were washed 3 times with iced PBS containing 0.2% BSA, and pellets obtained by centrifugation at 500×g for 10 min were counted using a $\gamma$-counter.

Cyclic AMP Production

The concentration of cAMP in lysates of MLO-Y4 cells upon treatment with sCT was determined using a kit based on the competition for a fixed amount of anti-cAMP antibody between unlabeled cAMP present in the sample and peroxidase-labeled cAMP (Amersham Pharmacia Biotech, Arlington Heights, Ill.).

Glucocorticoid Administration to Mice

Male Swiss Webster mice (Charles River Laboratories, Stone Ridge, N.Y.) were given daily subcutaneous injections of 0.75 mg/kg/d of alendronate dissolved in saline (4-amino-1-hydroxybutylidene-1,1-bisphosphonate, obtained from C. W. G. M. Löwik, University Hospital, Leiden, the Netherlands) beginning 3 days before subcutaneous implantation of 2.1 mg/kg/day pellets of slow-release prednisolone (Innovative Research of America, Sarasota, Fla.). To adjust for the difference in the metabolic rate in mice compared to that in humans, the daily glucocorticoid dose was divided by the metabolic weight, i.e. the weight in kg to the 3/4 power (Borchard, et al., 1992. Drug dosage in laboratory animals: a handbook. CRC Press, Inc., Boca Raton, Fla. 514 pp.; Kleiber, M. 1961. The fire of life: an introduction to animal energetics. New York). Expressed in this manner, 2.1 mg/kg/day of prednisolone is 0.0735 mg/day given to a 0.035 kg mouse or 0.909 mg/kg$^{3/4}$, a value quite similar to 0.926 mg/kg$^{3/4}$ which results when a dose of 20 mg/day of prednisolone is given to a 60 kg human. One control group received saline injections with placebo pellet implantation while another group received saline injections plus prednisolone pellets. Dual-energy X-ray absorptiometry (DEXA) was used to determine spinal bone mineral density (spinal BMD) at the end of the 56-day experiment, as previously described (Weinstein et al., 1998. *J. Clin. Invest.* 102:274–282).

Measurement of Apoptosis in Undecalcified Bone Sections

Sections of vertebral bone (L1 to L5) were mounted on silane-coated glass slides (Scientific Device Lab, Inc., Des Plaines, Ill.), deplasticized and incubated in 10 mM citrate buffer, pH 7.6, in a microwave oven at 98° C. for 5 minutes (Jilka, et al., 1998. *J. Bone Miner. Res.* 13:793–802). Slides were then incubated with 0.5% pepsin for 30 minutes at 37° C. Apoptotic cells were detected by the TUNEL reaction as described above using 0.15% $CuSO_4$ for color enhancement of the diaminobenzidine in sections counterstained with 1% methyl green. The TUNEL reaction is noted within cell nuclei and the cells whose nuclei were clearly brown from the streptavidin-horse radish peroxidase conjugate instead of blue-green from the methyl green were interpreted as positive. Plastic-embledded sections of weaned rat mammary tissue were used as a positive control. Negative controls were made by omitting the transferase from the TUNEL reaction. Morphological changes characteristic of apoptosis were carefully examined to minimize ambiguity regarding the interpretation of results. With these precautions, TUNEL has been unequivocally associated with apoptosis and used with DNA fragmentation and immunohistochemical studies to demonstrate apoptosis of osteoblastic cells and osteoblasts both in vitro and in vivo (Weinstein et al., 1998. *J. Clin. Invest.* 102:274–282; Jilka, et al., 1998. *J. Bone Miner. Res.* 13:793–802). Osteocytes were identified inside lacunae in mineralized bone (FIG. 11A). Osteoblasts were identified as cuboidal cells lining the osteoid-covered trabecular perimeter (FIG. 11B).

In Vitro Bone Resporption Assay

Pregnant Swiss Albino mice were injected with 30 $\mu$Ci of $^{45}$Ca (1 Ci/mmol: Amersham, London, U.K.) on day 16 of gestation, whereby vaginal plug discovery is defined as day 0 of gestation. One day later, the animals are sacrificed by cervical dislocation. The $^{45}$Ca prelabeled fetal metacarels were excised in HEPES-buffered Hank's solution (pH 7.4). Cultures were performed in $\alpha$-MEM+10% heat inactivated FCS in a final volume of 250 $\mu$l. The bones were preincubated for 24 h to allow calcium exchange with the medium to reach a steady state. The explants were treated with bisphosphonate during this 24 h period and then cultured for 10 days in the absence of bisphosphonate. The culture medium was refreshed every 3–4 days. All cultures were performed at 37° C. in a humidified atmosphere of 5% $CO_2$. At the end of culture, residual $^{45}$Ca was extracted from the bones in 0.5 ml of 5% trichloroacetic aced (TCA) for 24 h.

Calculation of Osteoclastic Resorption

Resorption was expressed as a percentage of $^{45}$Ca in the prelabeled explant that is released in the medium during culture (% $^{45}$Ca-release). The values were corrected for physicochemical calcium exchange by subtraction of the % $^{45}$Ca-release from a dead bone (% KCo) (=% net $^{45}$Ca-release). Bones were "killed" by three cycles of freeze-thawing. Osteoclastic resporption is thus calculated as: % net $^{45}$Ca-release=[$^{45}$Ca-release into medium (cpm)/total $^{45}$Ca incorporated in bone (cpm)] X 100%-% KCO release.

In Vivo Bone Resporption Assay

Groups of 5-week-old female Swiss Ali no mice are injected subcutaneously with a bisphosphonate. Each group is comprised of five mice. After daily treatment for 12 days, the mice are sacrificed by cervical dislocation, and their tibiae are removed and freed of adjacent tissue and their length measured. Subsequently, the bones are dried at 37° C. for 5 days. Each bone is then cut 3.5 mm from the proximal end to separate the epiphysis and metaphysis in one piece from the diaphyseal region. The dry weights of the bone fragments are then determined. Results are expressed as means ±S.E.M. Differences between numbers are examined by one-way analysis of variance for multiple comparisons followed by Fisher's test.

Statistical Analysis

Figure 5A:
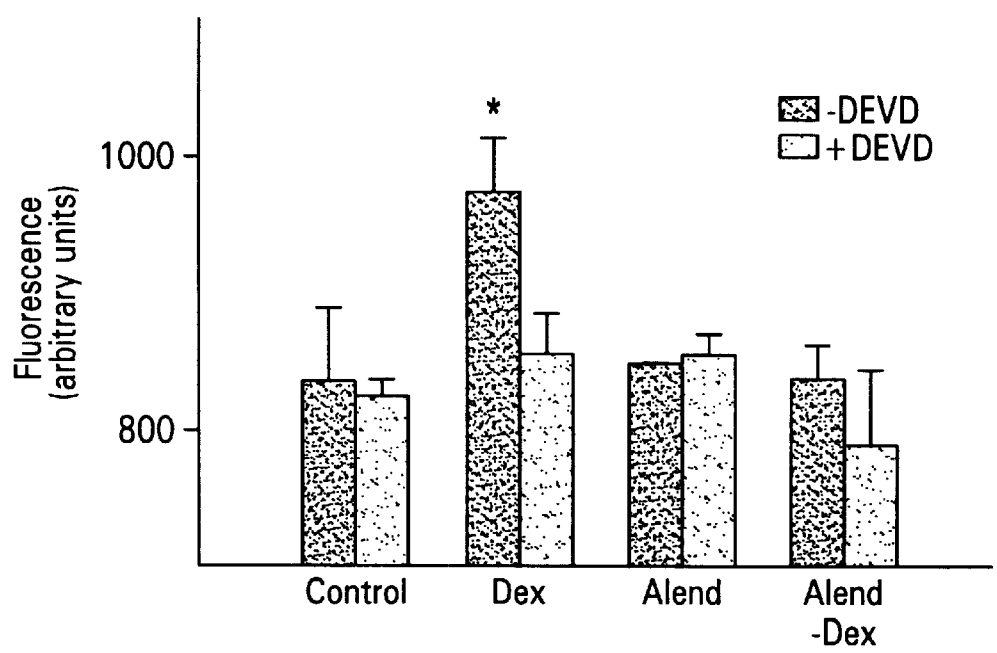
FIGS. 5A and 5B are bar graph plots demonstrating that bisphosphonates inhibit the increase in caspase-3 activity and the decrease in the number of living cells induced by dexamethasone.

Data were analyzed by one-way analysis of variance (ANOVA), and the Student-Neuman-Keuls method was used to estimate the level of significance of differences between means. The effect of bisphosphonates on the proportion of MLO-Y4 cells exhibiting chromatin condensation and/or nuclear fragmentation in the absence of dexamethasone (FIG. 3) was also analyzed using exact chi-square tests, adjusting the p-values within each experiment using a Bonferroni correction and stratifying by experiment when combining information across experiments. All p-values were compared to an a value of 0.05 to determine significance. Data of Table I were also analyzed by exact chi-square test. In order to establish whether the effect of BPs was dependent on the pro-apoptotic agent used, data of FIGS. 5 and 6 were analyzed by two-way ANOVA, in which the two variables were the proapoptotic agents (dexamethasone, etoposide, and TNF-$\alpha$) and the pretreatments (vehicle, alendronate and IG-9402). Subsequently, the Student-Newman-Keuls method was used to estimate the significance of the differences among pretreatments.

The present invention is directed towards treatments that induce osteocyte-specific apoptosis in patients in need of such treatment.

The present invention is also directed towards methods of screening for antifracture compounds with osteocyte-specific apoptosis activity.

VIII. Illustrative Examples

The following examples are given for the purpose of illustrating various embodiments of the invention and are not meant to limit the present invention in any fashion.

As one example, 17$\beta$-estradiol, the synthetic steroid estratriene-3-ol, which is a potent neuroprotective compound, and 17$\alpha$-estradiol, have potent anti-apoptotic effects on osteoblastic cells in vitro and osteocytic cells.

U.S. Pat. No. 5,843,934 to Simpkins discloses that an estrogen having insubstantial sex-related activity, and in particular, $\alpha$-estrogens such as 17$\alpha$-estradiol, can be administered to a patient to retard the adverse effects of osteoporosis in a male or female. The '934 patent does not address how to select a compound to increase bone mass opposed to treat osteoporosis. Increasing bone mass is a different indication from the treatment of bone loss, as dramatically illustrated by the fact that the U.S. Food and Drug Administration has approved a number of drugs for the treatment of osteoporosis, but has not approved any drugs to date as bone anabolic agents.

17$\beta$-Estradiol is used in these illustrative examples even though it is a potent activator of estrogen-like gene transcription, because it tightly binds to the estrogen receptor and inhibits osteoblastic and osteocytic apoptosis. The compound must be modified to fall within the selection criteria for the present invention by altering it in such a way that it cannot enter the cell to induce gene transcription. Such modifications can occur, for example, by covalently attaching, either directly or through a linking moiety, a second moiety that prevents or limits cell penetration. Any other estrogen or androgen that binds appropriate to the relevant receptor can be likewise modified for use to increase bone mass.

It is noteworthy that (a) the anti-apoptotic effect of 17$\beta$-estradiol on both osteoblasts and osteocytes are reproduced with a membrane impermeable 17$\beta$-estradiol—BSA conjugate; (b) the anti-apoptotic effects of these compounds are diminished by ICI 182780, a pure estrogen receptor antagonist; and (c) that the antiapoptotic effects of all these compounds cannot be shown in HeLa cells unless these cells are stably transfected with either the estrogen receptor $\alpha$ or the estrogen receptor $\beta$.

The following examples are given for the purpose of illustrating various embodiments of the invention and are not meant to limit the present invention in any fashion.

EXAMPLE 1

Antiresorptive agents such as BPs and calcitonin, as well as estrogen, decrease fracture incidence disproportionally to their effect on bone mass. This suggests an additional effect on bone strength unrelated to effects on bone mineral density (BMD). Disruption of the osteocyte network could compromise this mechanism, leading to microdamage accumulation and increased bone fragility. Such a defect in bone quality could account for the higher incidence of fractures in glucocorticoid-treated patients compared with postmenopausal women, even though BMD in the former is relatively higher.

To determine the role of osteocyte apoptosis in bone disease, apoptosis was induced in the osteocytic cell line MLO-Y4 by exposing osteocytes to concentrations of etoposide, TNF-α, and dexamethasone as shown in FIG. 1A. MLO-Y4 cells were incubated for 1 h in vehicle or 50 nM DEVD-CHO. Subsequently, etoposide, TNF-α, or dexamethasone (Dex) were added at final concentrations of 50 μg/ml, 1 nM, or $10^{-6}$ M, respectively, and cells were incubated for additional 6 h. Dead cells were enumerated by trypan blue uptake.

Figure 1B:
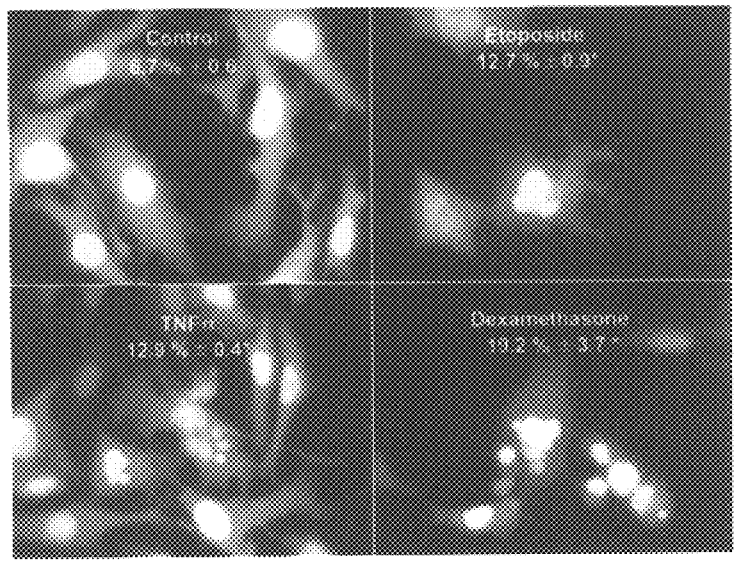

Apoptosis induced in osteocytes was confirmed by fluorescent microscopy using MLO-Y4 cells stable transduced with green fluorescent protein. FIG. 1B shows characteristics of apoptosis including chromatin condensation and nuclear fragmentation. MLO-Y4 cells stably transduced with GFP were maintained for 6 h in the presence of vehicle, 50 μM etoposide, 1 nM TNF-α, or $10^{-6}$ M dexamethasone. Numbers indicate the percentage of cells undergoing apoptosis, as determined by evaluating the nuclear morphology of>500 cells in fields selected by systematic random. Results are means ±S.D. of three independent experiments. Original magnification: 400×. Data were analyzed by one-way ANOVA. * indicates P<0.05 versus control (Student-Newman-Keuls method).

The results depicted in FIG. 1A demonstrate that exposure of MLO-Y4 osteocytic cells to the glucocorticoid dexamethasone ($10^{-6}$ M) increased the percentage of cells stained with trypan blue. As in other in vitro systems (Reichardt, et al., 1998. DNA binding of the glucocorticoid receptor is not essential for survival *Cell* 93:531–541; Chauhan, et al., 1997. *Oncogene* 15:837–843; Clevenger, et al., 1997. *Mol. Endocrinol.* 11:608–618), pro-apoptotic effects of dexamethasone were also obtained with concentrations between $10^{-7}$ and $10^{-5}$ M. A similar effect was obtained with the inhibitor of DNA repair etoposide, which blocks topoisomerase II activity (Stefanelli, et al., 1998. *Biochem. J.* 332:661–665), and with TNF-α, an activator of death receptors (Ashkenazi, A. and V. M. Dixit. 1998. *Science* 281:1305–1308). The increase in cell membrane permeability detected by trypan blue was prevented by DEVD-CHO, a specific inhibitor of caspases which trigger death by apoptosis (Thornberry, et al., 1998. Caspases: enemies within. *Science* 281:1312–1316) (FIG. 1A). Consistent with this finding, all the pro-apoptotic agents used here induced an increase in the percentage of cells exhibiting the sine qua non features of apoptosis, i.e., chromatin condensation and nuclear fragmentation, as shown by microscopic examination of MLO-Y4 cells stable transduced with nuclear green fluorescent protein (FIG. 1B).

EXAMPLE 2

Figure 2:
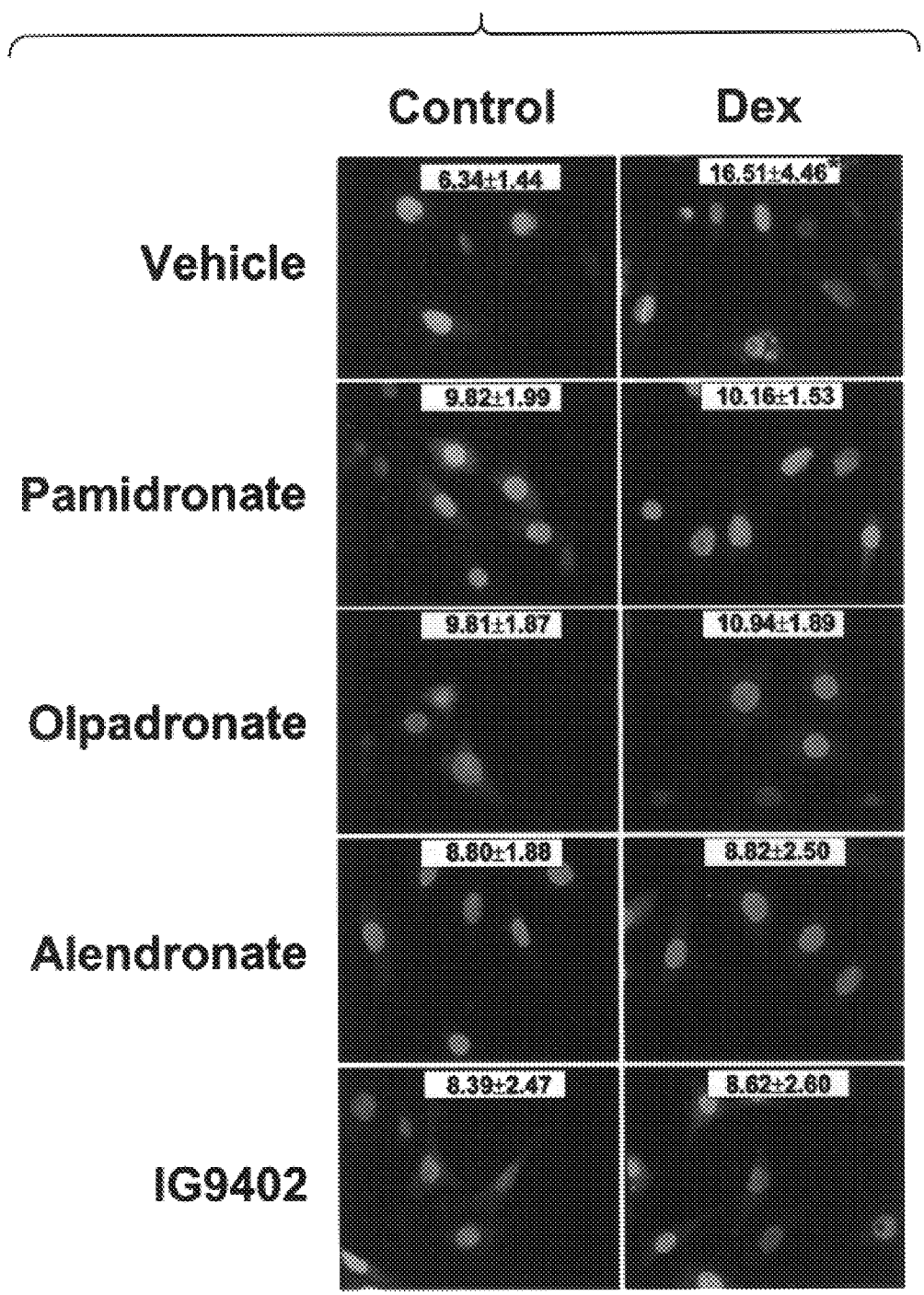
FIG. 2 is a series of fluorescent micrographs demonstrating that biphosophonates inhibit glucocorticoid-induced apoptosis of osteocytes.

Prevention of glucocorticoid-induced apoptosis by bisphosphonates was confirmed by examining the nuclear morphology of MLO-Y4 cells stably transduced with nuclear GFP shown in FIG. 2. MLO-Y4 cells stably transduced with GFP were treated for 1 h with $10^{-7}$ M concentration of the indicated bisphosphonates, followed by addition of $10^{-6}$ M dexamethasone. After 6 h, cells were fixed. The cells were evaluated under a fluorescent microscopy. Numbers indicate the percentage of cells undergoing apoptosis as determined by evaluating the nuclear morphology of>500 cells in fields selected by systematic random in at least three different experiments (mean ±S.D.). Original magnification: 400×. Data were analyzed by one-way ANOVA. * indicates P<0.05 versus control (Student-Newman-Keuls method). The effect of bisphosphonates on the proportion of MLO-Y4 cells exhibiting chromatin condensation and/or nuclear fragmentation in the absence of dexamethasone was also analyzed using exact chi-square tests in three experiments with pamidronate, olpadronate, or IG-9402, and six experiments with alendronate. Bonferroni adjusted pair-wise comparisons between untreated groups and groups treated with bisphosphonates yielded no significant differences.

The small (2–3%) increase in cells exhibiting chromatin condensation and/or nuclear fragmentation observed in BP-treated cultures compared to untreated cultures was not reproduced by trypan blue uptake and was not inhibited by DEVD (not shown), indicating that it was not due to apoptosis. Treatment with bisphosphonates for 6 or 24 h did not increase the total number of MLO-Y4 cells. However, the possibility that these agents stimulate osteocytic cell division, cannot be excluded as it has been demonstrated for other osteoblastic cell preparations in vitro (Giuliani, et al., 1998. *Bone* 22:455–461). This could cause an increase in the number of cells with 2 nuclei that could have been scored as exhibiting nuclear fragmentation.

EXAMPLE 3

Figure 4:
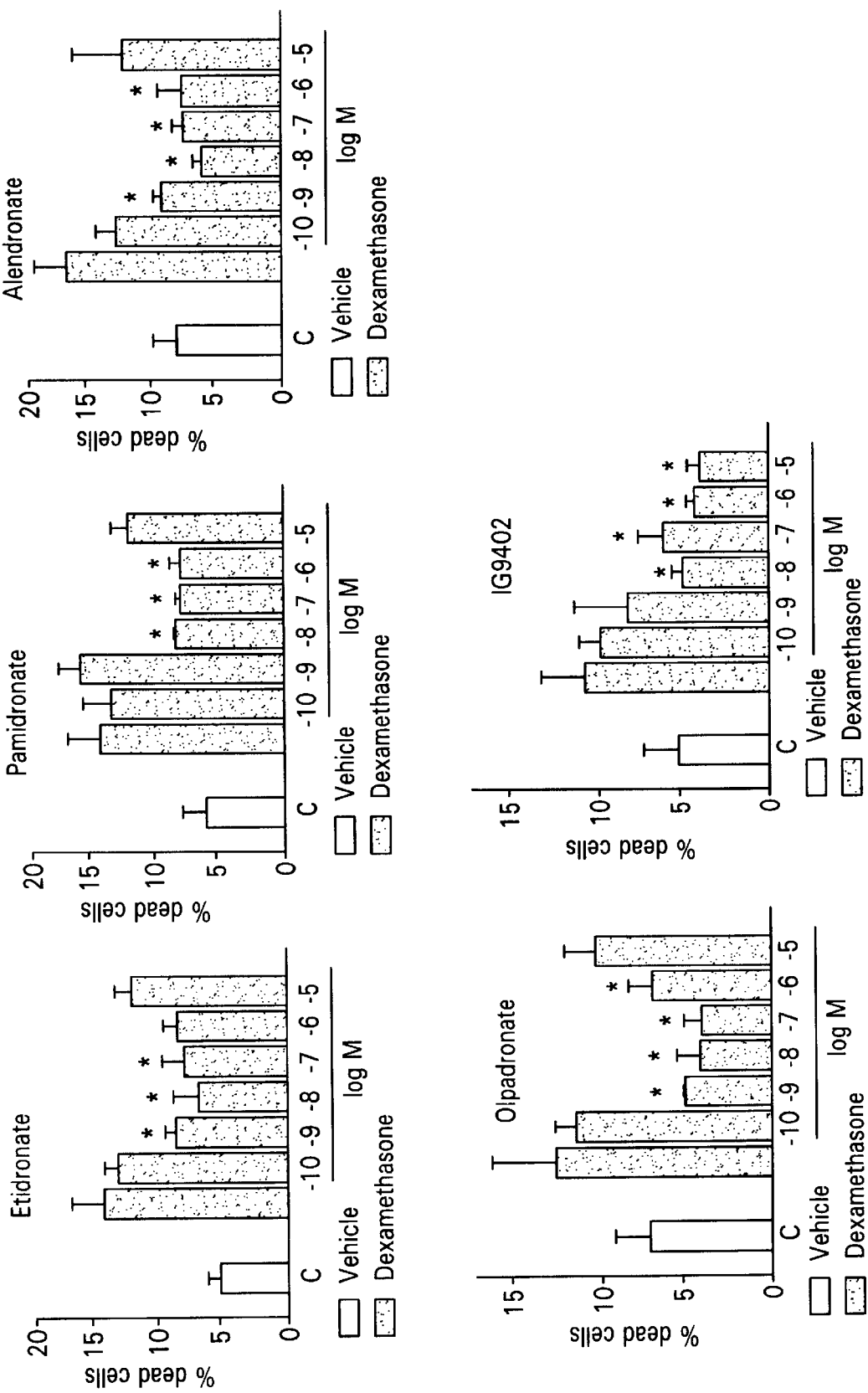
FIG. 4 is a series of bar graph plots demonstrating that bisphophonates inhibit glucocorticoid-induced apoptosis of osteocytic cells.

Prevention of glucocorticoid-induced apoptosis by bisphosphonates was investigated. FIG. 4 shows that pretreatment with bisphosphonates for 1 h before addition of dexamethasone inhibited glucocorticoid-induced apoptosis, with minimal effective concentrations between $10^{-9}$ and $10^{-8}$ M. MLO-Y4 cells were pretreated with the indicated concentrations of BPs for 1 h, and subsequently dexamethasone ($10^{-6}$ M final concentration) was added for 6 hours. The percentage of dead cells was determined by trypan blue uptake, as in Methods and Materials. Bars represent the mean ±S.D. of three independent measurements. Data were analyzed by one-way ANOVA. * indicates P<0.05 versus dexamethasone alone (Student-Newman-Keuls method).

At concentrations higher than $10^{-6}$ M this inhibitory effect was decreased or lost. Comparable responses were obtained with etidronate and with the aminobisphosphonates alendronate, pamidronate, or olpadronate. Similar biphasic effects of bisphosphonates on osteoblastic cell preparations have been previously described (Giuliani, et al., 1998. *Bone* 22:455–461; Giuliani, et al., 1995. *J. Bone Min. Res.* 10 (suppl):S171(Abstr.); Tenenbaum, et al., 1992. *Bone* 13:249–255).

Interestingly, amino-olpadronate (IG-9402), a compound that lacks anti-resorptive activity (van Beek et al., 1998. *J. Bone Miner. Res.* 11:1492–1497), was also effective. However, unlike the other BPs, the inhibitory effect of IG-9402 persisted at high concentrations. Removal of BPs before inducing apoptosis or addition of BPs simultaneously with dexamethasone also prevented the effect of the pro-apoptotic agent (not shown). Exposure of MLO-Y4 cells to $10^{-10}$ to $10^{-3}$ M alendronate or IG-9402 in the absence of pro-apoptotic stimuli did not affect cell viability (not shown).

EXAMPLE 4

Figure 5B:
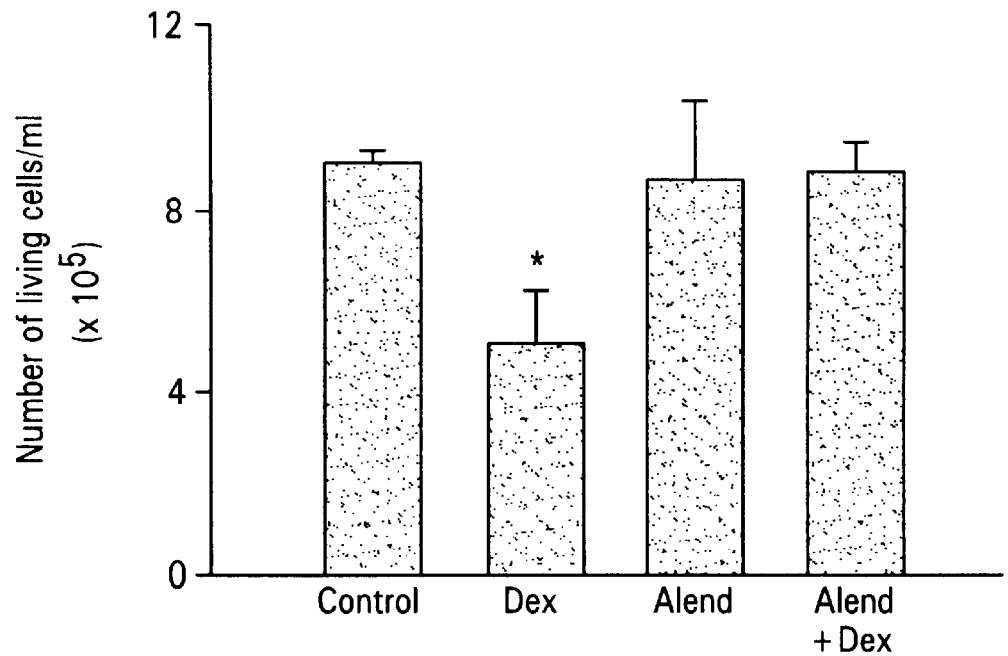

Consistent with an anti-apoptotic action of bisphosphonates, alendronate inhibited the dexamethasone-induced increase in caspase-3 activity (FIG. 5A) and in the number of TUNEL positive cells (Table I). Likewise, 24 hour-treatment with dexamethasone decreased significantly the number of living MLO-Y4 cells (as determined by trypan blue uptake) and alendronate abolished this effect (FIG. 5B). MLO-Y4 cells were incubated with vehicle or $10^{-7}$ M alendronate for 1 h. Subsequently, dexamethasone was added to reach a final concentration of $10^{-6}$ M and cells were cultured for 16 h (FIG. 5A) or 24 h (FIG. 5B). Caspase-3 activity was determined by measuring the degradation of the fluorometric substrate DEVD-AFC in the absence or presence of the irreversible inhibitor DEVD-CHO, as detailed in Example 5. Cells were harvested by trypsinization and the number of living cells was scored using an hemocytometer as described below. Bars represent the mean ±S.D. of three independent measurements. * indicates $P<0.05$ versus control, by ANOVA (Student-Newman-Keuls method).

Alendronate alone, i.e., in the absence of the pro-apoptotic stimulus of dexamethasone, did not affect any of these parameters.

TABLE I

Effect of dexamethasone and alendronate on apoptosis of osteocytic MLO-Y4 cells.

| | Number of TUNEL positive cells | number of TUNEL negative cells | % of TUNEL positive cells |
|---|---|---|---|
| Control | 31 | 490 | 5.95 |
| Dexamethasone | 66 | 490 | 11.87* |
| Alendronate | 35 | 533 | 6.16 |
| Dexamethasone + Alendronate | 35 | 507 | 6.46 |

MLO-Y4 cells were treated for 1 h with $10^{-7}$ M alendronate or vehicle, followed by addition of dexamethasone to reach $10^{-6}$ M. After 6 h, cells were fixed and the TUNEL reaction was performed as detailed in Methods. Data were obtained by counting>500 cells in fields selected by systematic random sampling. * $P<0.001$ versus control by exact chi-square, adjusting the p-value using the Bonferroni correction.

EXAMPLE 5

Figure 3:
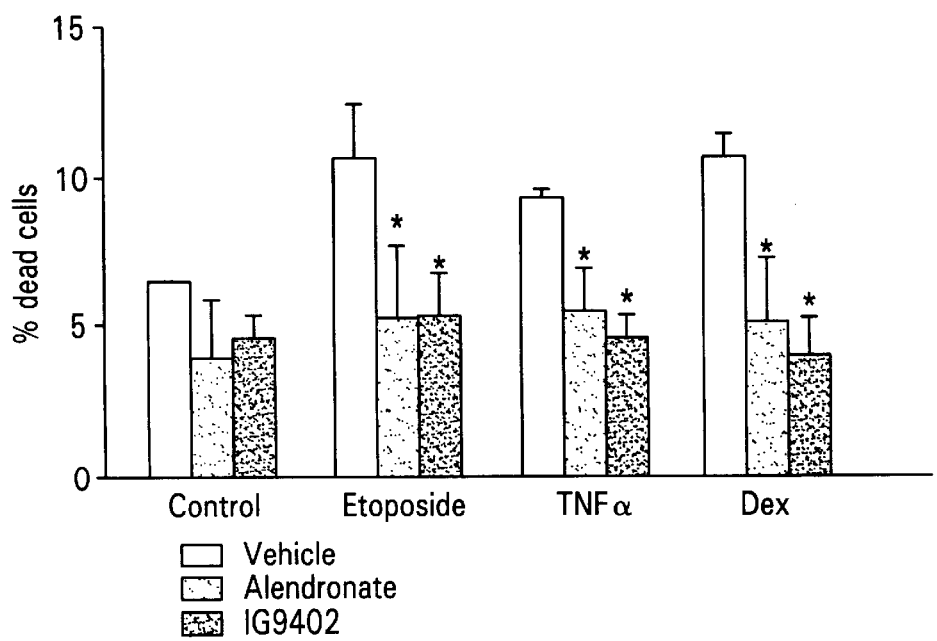
FIG. 3 is a series of bar graph plots demonstrating that the protective effect of bisphosphonates on osteocytic or osteoblastic cells is independent of the pro-apoptotic stimulus.
Figure 3:
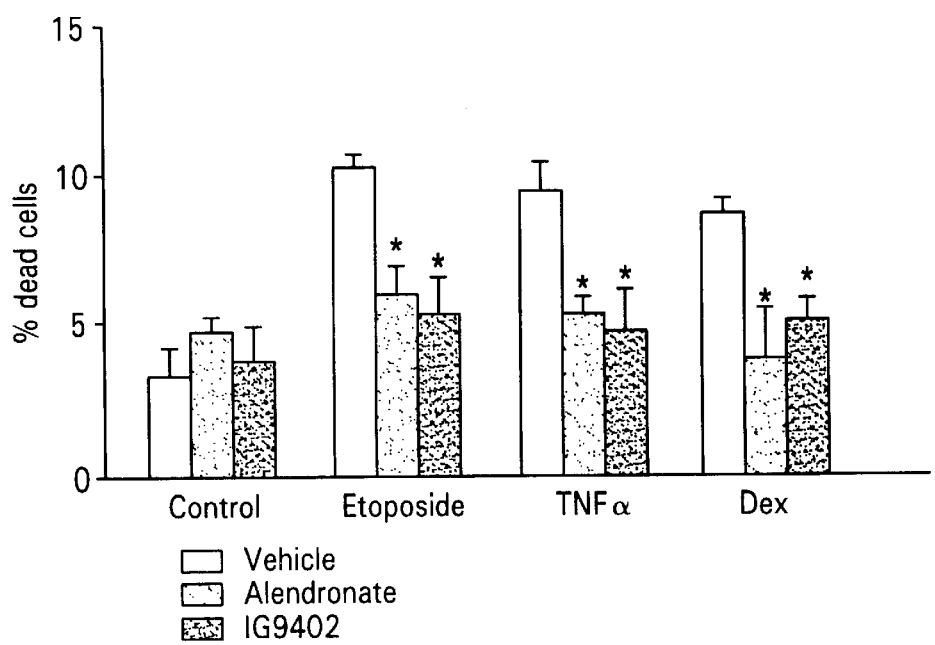

Pretreatment with alendronate or IG-9402 also prevented apoptosis of MLO-Y4 cells induced by either etoposide or TNF-α (FIG. 3). MLO-Y4 cells were incubated with vehicle, $10^{-7}$ M alendronate or IG-9402 for 1 h. Subsequently, etoposide, TNF-α, or dexarnethasone were added to reach final concentrations of 50 μg/ml, 1 nM, or $10^{-6}$ M, respectively, and cells were cultured for 6 h, as in FIG. 1. The percentage of dead cells was determined by trypan blue uptake. Bars represent the mean ±S.D. of three independent measurements. Data were analyzed by two-way ANOVA. No interaction between the proapoptotic agents and the pretreatments was found (at a α-level of 0.05). * indicates $P<0.05$ versus etoposide, TNF-α, or dexamethasone alone (Student-Newman-Keuls method).

In full agreement with an earlier observations (Jilka, et al., 1998. *J. Bone Miner. Res.* 13:793–802; Jilka, et al., 1999. *J. Clin. Invest.* 104:439–446), dexamethasone-, TNF-α- and etoposide-induced apoptosis of osteoblastic cells derived from murine calvaria. Osteoblastic cells derived from murine calvaria were incubated with vehicle, $10^{-7}$ M alendronate or IG-9402 for 1 h. Subsequently, etoposide, TNF-α, or dexamethasone were added to reach final concentrations of 50 μg/ml, 1 mM, or $10^{-6}$ M, respectively, and cells were cultured for 6 h, as in FIG. 1. The percentage of dead cells was determined by trypan blue uptake. Bars represent the mean ±S.D. of three independent measurements. Data were analyzed by two-way ANOVA. No interaction between the proapoptotic agents and the pretreatments was found (at a α-level of 0.05). * indicates $P<0.05$ versus etoposide, TNF-α, or dexamethasone alone (Student-Newman-Keuls method).

Similar to their effect on osteocytic cells, alendronate and IG-9402 inhibited apoptosis of osteoblastic cells induced by all these agents. No statistical interaction was found between the proapoptotic agents and the different pretreatments (vehicle, alendronate and IG-9402) indicating that the inhibitory effect of bisphosphonates on osteocytes and osteoblasts was independent of the pro-apoptotic agent.

EXAMPLE 6

Figure 6A:
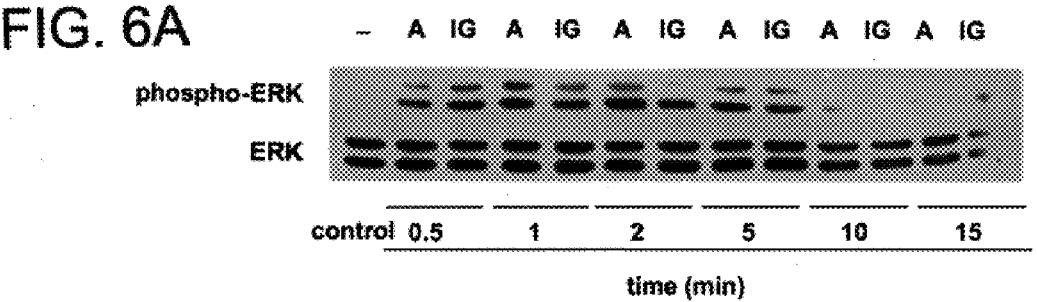
FIGS. 6A and 6B show the time course of ERK activation by Alendronate and IG-9402.
Figure 6B:
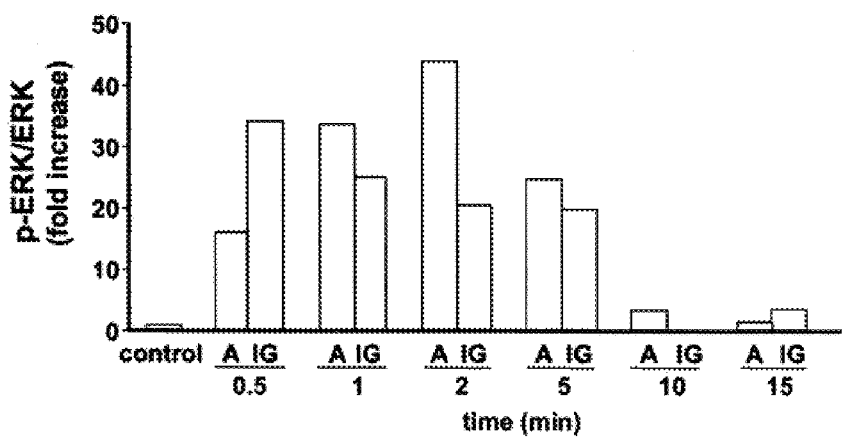

Anti-apoptotic agents in other cell systems transiently stimulate the phosphorylation of extracellular signal-regulated kinases (ERKs), members of the MAP kinase family which enhance cell survival (Xia, et al.,. 1995. *Science* 270:1326–1331; Gardner, et al., 1996. *J. Biol. Chem.* 271:14560–14566; Wang, et al., 1998. *Biochem. J.* 333:291–300). To determine the mechanism of the anti-apoptotic effect of bisphosphonates, whether bisphosphonates influenced ERK activation in MLO-Y4 osteocytic cells was examined. FIG. 6 shows that alendronate and IG-9402, at $10^{-7}$ M, induced a rapid and transient increase in the phosphorylation of ERK 1 and 2. This effect was observed as early as 0.5 min, reached a maximum at 1–2 min, and decreased to basal levels by 15 min (FIG. 6A). The levels of total ERKs did not change upon treatment (FIG. 6B). The data show that the mechanism of the antiapoptotic effect of BPs involves activation of extracellular signal regulated kinases (ERKs).

EXAMPLE 7

Figure 7A:
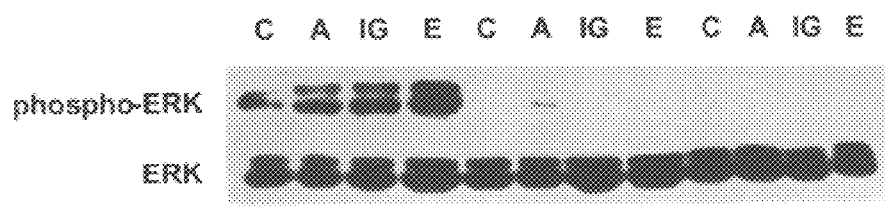
FIG. 7A is an autoradiogram demonstrating that pretreatment of osteocytes with PD98059 and UO126 inhibits BP induced ERK phosphorylation. Cells were incubated for 23 min with vehicle, 50 μM PD98059 or 1 μM UO126 before addition of $10^{-7}$ M alendronate (A), IG-9402 (IG), or etidronate (E) for 2 min. Cell lysates were obtained and assayed for the presence of phosphorylated ERK1/2 as in FIG. 6.
Figure 7B:
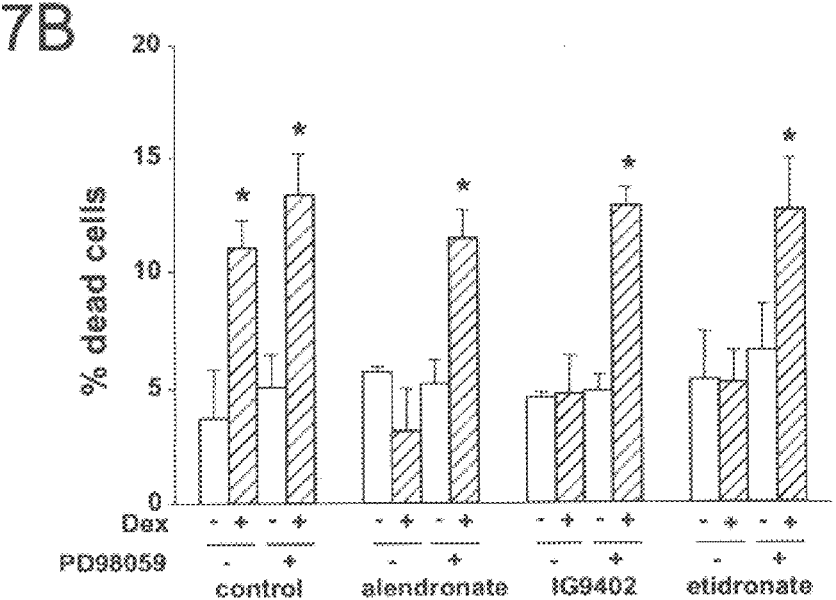
FIGS. 7B and 7C are bar graph plots demonstrating that activation of ERKs in osteocytes is required for the antiapoptotic effect of BPs. Cells were treated for 30 min with PD98059 (FIG. 7B) or with UO126 (FIG. 7C), followed by addition of $10^{-7}$ M bisphosphonates. After 1 h, $10^{-6}$ M dexamethasone was added and cultures incubated for 6 h. The percentage of apoptotic cells was determined by trypan blue exclusion, as in FIG. 1A. Bars represent the mean ±S.D. of three independent measurements. * indicates P<0.05 versus control by one-way ANOVA (Student-Newman-Keuls method).
Figure 7C:
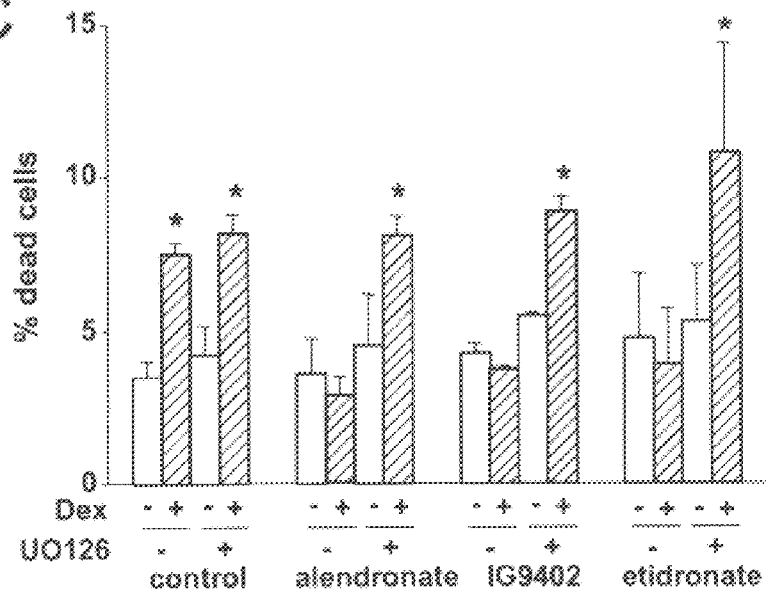

FIG. 7A shows an increase in the phosphorylated fraction of ERKs induced by etidronate. As expected, bisphosphonate-induced phosphorylation of ERKs was abolished by pretreatment of the cells with PD98059 or by U0126, specific inhibitors of mitogen-activated protein kinase kinase (Alessi, et al., 1995. *J. Biol. Chem.* 270:27489–27494; Favata, et al., 1998. *J. Biol. Chem.* 273:18623–18632) the kinase responsible for phosphorylation of ERKs (FIG. 7A). More importantly, pretreatment of MLO-Y4 cells with either PD98059 or U0126 abrogated the anti-apoptotic effect of alendronate, IG-9402, and etidronate (FIGS. 7B and 7C), demonstrating that activation of ERKs is required for the anti-apoptotic effect of these agents.

EXAMPLE 8

Because sCT is another anti-resorptive agent with anti-fracture properties, whether it also influenced apoptosis of cells of the osteoblastic lineage was investigated next. Previous evidence indicates the presence of calcitonin receptors in cells of the osteoblastic lineage, including osteoblastic cells from murine calvaria (Forrest et al., 1985. *Calcif. Tissue Int.* 37:51–56; Iida-Klein et al., 1992. *Endocrinology* 130:381–388; Farley et al., 1991. *Calcif. Tissue Int.*

48:297–301). To determine whether MLO-Y4 osteocytic cells expressed calcitonin receptors, a binding assay using intact cells was performed. UMR106-06 ositeoblastic cells were used as a positive control. Like UMR106 cells, MLO-Y4 cells exhibited binding of $^{125}$I-sCT that could be effectively competed by an excess of unlabeled sCT. Consistent with the presence of specific binding, treatment of MLO-Y4 cells with sCT induced an increase in the intracellular levels of cAMP.

Figure 8:
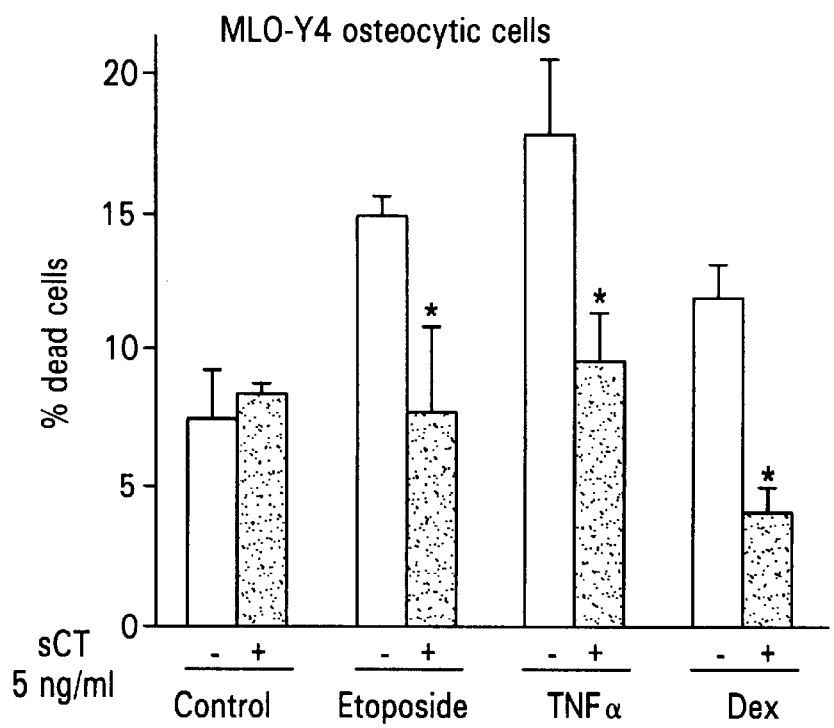
FIG. 8 is a series of bar graph plots showing that salmon calcitonin inhibits glucocorticoid-, TNF-α- and etoposide-induced apoptosis of MLO-Y4 and osteoblastic cells. MLO-Y4 osteocytic cells or osteoblastic cells were treated with sCT for 1 h before the addition of the pro-apoptotic stimuli. The percentage of dead cells was determined by trypan blue uptake as described in FIG. 1A. Bars represent the mean ±S.D. of three independent measurements. * indicates P<0.05 versus etoposide, TNF-α, or dexamethasone alone by one-way ANOVA (Student-Newman-Keuls method).
Figure 8:
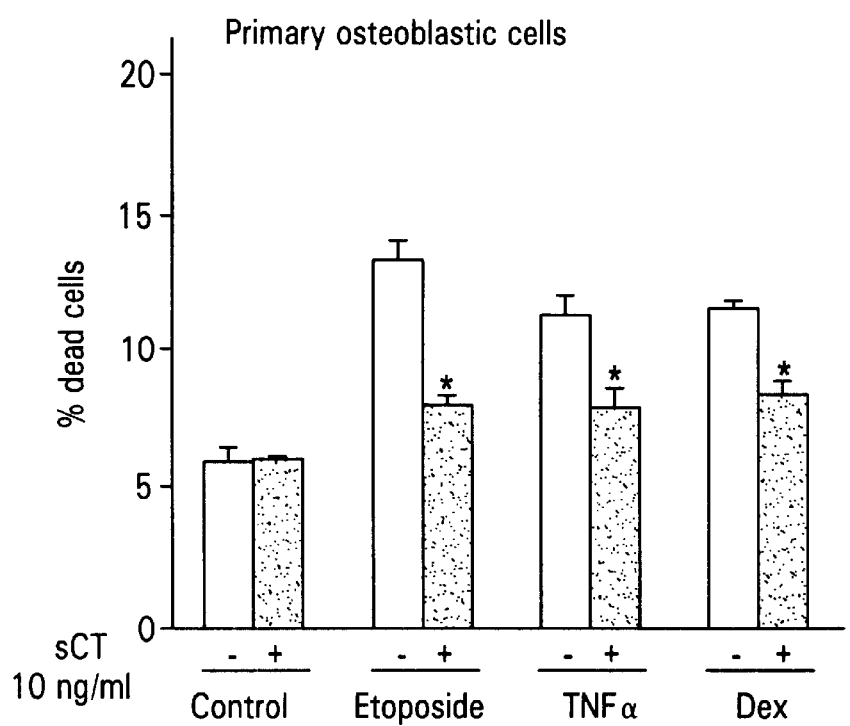
Figure 9A:
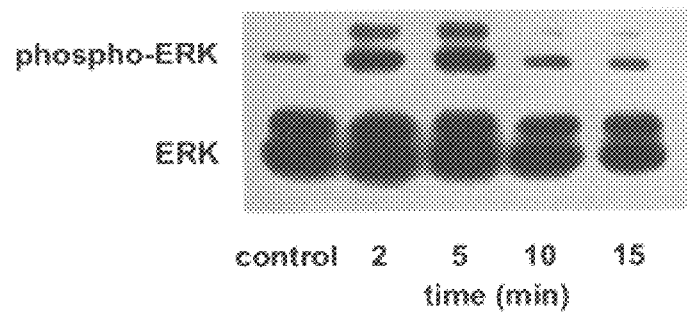
FIGS. 9A and 9B consist of an autoradiograph and bar graph plot respectively, and they show that the anti-apoptotic effect of salmon calcitonin involves ERK activation.
Figure 9B:
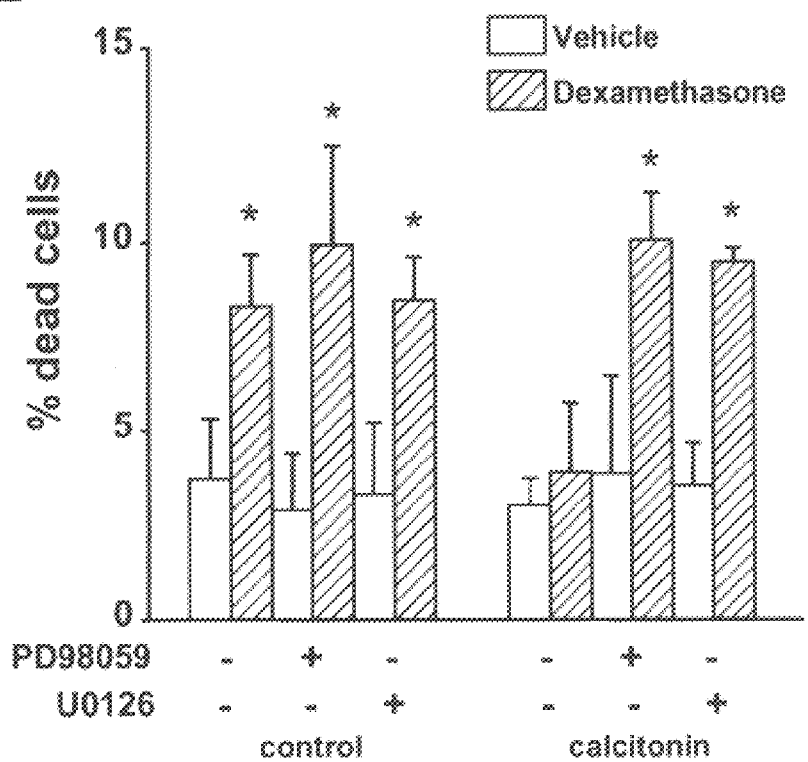

As in the case of BPs, pretreatment of MLO-Y4 or osteoblastic cells with 5–10 ng/ml (1.45–2.90 nM) sCT prevented apoptosis induced by etoposide, TNF-α, or glucocorticoids (FIG. 8). Further, sCT induced a rapid and transient increase in the phosphorylation of ERKs in MLO-Y4 cells. This effect was maximum at 5 min and decreased to basal levels by 15 min (FIG. 9A). In addition, and as in the case of BPs, the prevention of MLO-Y4 cell apoptosis by sCT was abolished by pretreatment with either inhibitor of ERK activation, PD98059 or U0126 (FIG. 9B).

EXAMPLE 9

To address the significance of these in vitro studies, the effect of alendronate administration was examined in a murine model of glucocorticoid excess-induced apoptosis of osteocytes and osteoblasts (Weinstein et al., 1998. *J. Clin. Invest.* 102:274–282). As previously shown, administration of prednisolone decreased spinal BMD and increased the prevalence of osteoblast apoptosis in vertebral cancellous bone (Table II). The increase in cancellous osteocyte apoptosis did not, however, reach significance. The higher rate of remodeling in cancellous compared with cortical bone probably did not allow the high accumulation of apoptotic osteocytes that had noted previously in femoral metaphyseal cortical bone (Weinstein et al., 1998. *J. Clin. Invest.* 102:274–282). Nonetheless, administration of alendronate, beginning 3 days before the implantation of prednisolone pellets, prevented the bone loss and abolished the increase in bone cell apoptosis induced by the glucocorticoid.

The prevalence of apoptotic osteoblasts detected in this experiment by the TUNEL reaction with $CuSO_4$ enhancement in bone sections is higher than the values obtained in previous studies using TUNEL without $CuSO_4$ (Weinstein et al., 1998. *J. Clin. Invest.* 102:274–282; Jilka, et al., 1998. *J. Bone Miner. Res.* 13:793–802). This is consistent with the contention that the enhancer allows cells undergoing the DNA degradation phase to be seen at an earlier stage. Prolongation or shortening of the time that apoptosis can be observed in a specimen, as a result of using more- or less-sensitive detection methods, influences the prevalence of the phenomenon (Jilka, et al., 1999. *J. Clin. Invest.* 104:439–446). Considering that in murine vertebral cancellous bone the wall width (W.Wi) is ~15 µm and the mineral appositional rate (MAR) is ~1.25 µm/day, the active lifespan of an osteoblast (W.Wi/MAR) is 12 days (288 h) (Weinstein et al., 1998. *J. Clin. Invest.* 102:274–282; Weinstein et al., 1997. *Endocrinology* 138:4005–4012; Jilka et al., 1996. *Journal of Clinical Investigation* 97:1732–1740). If the ratio between the duration of apoptosis ($t_{Ap}$) and the active lifespan of an osteoblasts (288 h) equals the prevalence of osteoblast apoptosis divided by the fraction of total osteoblasts that undergoes apoptosis at a given time ($f_{Ap}$), estimated to be between 0.5 and 0.7 (Parfitt A. 1990 Bone-forming cells in clinical conditions. In Bone. Vol. 1. The osteoblast and osteocyte. B. Hall, editor. CRC Press, Boca Raton, Fla. 351–430), then the prevalence of osteoblast apoptosis of 11.34% that we found in the placebo group (Table II) indicates that the duration of apoptosis recognized by this technique is between 46 to 65 h. This is consistent with previous reports estimating the TUNEL-labeled phase of apoptosis from as little as 1.5 h to as much as 48 h, depending on the sensitivity of the technique employed Bursch, et al., 1990. *Carcinogenesis* 11:847–853; Pompeiano, et al., 1998. *Cell Death Differ.* 5:702–709).

TABLE II

Effect of alendronate on BMD and the prevalence of osteocyte and osteoblast apoptosis in murine vertebral cancellous bone.

| measurement | placebo | prednisolone | prednisolone + alendronate |
|---|---|---|---|
| Apoptotic osteocytes (%) | 2.02 ± 0.70 | 2.37 ± 0.87 | 1.14 ± 0.22* |
| Apoptotic osteoblasts (%) | 11.34 ± 4.02 | 19.79 ± 5.17# | 10.88 ± 3.62* |
| Spinal BMD (% change) | −5.02 ± 0.34 | −12.48 ± 3.77# | −5.46 ± 3.52* |

Data shown are the mean ±SD from four to eight animals per group. * $P<0.05$ versus prednisolone alone, and * $P<0.05$ versus placebo, by ANOVA (Tukey test).

The results of the studies reported herein demonstrate that bisphosphonates inhibit osteocyte and osteoblast apoptosis, regardless of the pro-apoptotic stimulus used, indicating interference with a common pathway of apoptosis. These effects appear to be unrelated to the anti-resorptive properties of these agents, since IG-9402, a bisphosphonate that does not affect osleoclast activity (Van Beek, et al., 1998. *J. Bone Miner. Res.* 11:1492–1497), also exhibited anti-apoptotic properties on osteocytic cells and osteoblasts in the present studies. Moreover, the anti-apoptotic effects of bisphosphonates were shown with concentrations approximately 3 orders of magnitude lower than those required by the same agents for the promotion of osteoclast apoptosis in vitro (Hughes, et al., 1995. *J. Bone Miner. Res.* 10:1478–1487).

The inhibition of osteocytic and osteoblastic cell apoptosis in vitro was reproduced in vivo. Alendronate administration prevented the glucocorticoid-induced loss of bone and increased prevalence of osteocyte apoptosis in vertebral cancellous bone. Osteocyte experiments could have been performed in cortical bone, but osteocyte apoptosis is restricted to a narrow zone of the murine femoral metaphyseal cortex (Weinstein et al., 1998. *J. Clin. Invest.* 102:274–282).

To perform a more comprehensive investigation and avoid focal phenomena, the lumbar vertebrae 11 to 15 were examined. Vertebral cortical osteocyte apoptosis was absent, but apoptotic osteocytes and osteoblasts in the cancellous tissue were evenly distributed and, therefore, measured without bias. The prevalence of osteocyte and osteoblast apoptosis detected by the tunel assay is higher with than without the $CUSO_4$ as a color enhancer (Weinstein et al., 1998. *J. Clin. Invest.* 102:274–282; Jilka, et al., 1998. *J. Bone Miner. Res.* 13:793–802). Similar results were obtained in which a direct comparison between both procedures was performed (Jilka, et al., 1999. *J. Clin. Invest.* 104:439–446). This is consistent with the contention that the inclusion of $CuSO_4$ allows cells undergoing the DNA degradation phase to be seen at an earlier stage and thereby for a longer interval. Thus, the precise inventory of the fraction of apoptotic cells in bone varies depending on the identification technique and duration of the histologically recognizable features of a cell undergoing apoptosis.

The anti-apoptotic action of bisphosphonates on osteocytic cells and osteoblasts involved the rapid activation of ERKs. Indeed, rapid phosphorylation of ERKs by bisphosphonates was indispensable for the effects of bisphosphonates as their anti-apoptotic effects on osteocytic cells could be completely prevented by two specific inhibitors of ERKs activation, PD98059 and U0126. These findings are in full agreement with evidence that the ERK family of protein kinases is activated by several other anti-apoptotic agents (Xia, et al., 1995. Science 270:1326–1331; Gardner, et al., 1996. J. Biol. Chem. 271:14560–14566; Wang, et al., 1998. Biochem. J. 333:291–300).

In sharp contrast with the findings of the present report on osteoblasts and osteocytes, it is well established that bisphosphonates promote the apoptosis of mature osteoclasts in vitro and in vivo (Hughes, et al., 1995. J. Bone Miner. Res. 10:1478–1487). The pro-apoptotic action of bisphosphonates on this cell type is probably mediated via inhibition of the mevalonate pathway, which is responsible for the synthesis of lipids utilized in postranslational modification of proteins including prenylation (61). Based on this evidence it seems likely that bisphosphonates activate ERKs in osteoblastic cells in a ras-independent way, as ras activation and translocation to the membrane requires its prenylation (Luckman, et al., 1998. J. Bone Miner. Res. 13:581–589). Ras-independent activation of ERKs has been recently demonstrated for PTH (Verheijen, et al., 1997. J. Biol. Chem. 272:3423–3429). Whether the activation of ERKs by bisphosphonates is also ras-independent will require further studies.

Similar to bisphosphonates, the peptide hormone calcitonin inhibits osteocytic cells and osteoblast apoptosis, most likely via actions mediated by receptors linked to the adenylate cyclase system. These observations are in agreement with earlier findings indicating that agents that increase cAMP production, such as PTH and prostaglandins, suppress apoptosis of osteocytes/osteoblasts and periosteal cells, respectively (Jilka, et al., 1999. J. Clin. Invest. 104:439–446; Machwate, et al., 1998. Molecular Pharmacology 54:70–77). Therefore, it is likely that the protective effect of calcitonin on osteoblastic cells reported here i's also mediated via cAMP. Further, calcitonin-induced ERK phosphorylation was required for its anti-apoptotic effects on osteocytic cells.

The anti-apoptotic effects of bisphosphonates on osteoblasts and osteocytes demonstrated in this report are in the opposite direction to their effects on the survival of osteoclasts. Opposite effects on osteoclast and osteoblast apoptosis have also been demonstrated for TGF-$\beta$ (Jilka, et al., 1998. J. Bone Miner. Res. 13:793–802; Hughes, et al., 1996. Nat. Med. 2:1132–1136). Moreover, estrogen also inhibits osteocyte and osteoblast apoptosis while promoting apoptosis of osteoclasts (Hughes, et al., 1996. Nat. Med. 2:1132–1136). This remarkable phenomenon of opposing effects of such diverse classes of agents on osteoblast/osteocyte versus osteoclast apoptosis strongly suggests that the signaling pathways controlling the life span of these two bone cell types are inherently distinct.

Prolongation of the life span of osteocytes by bisphosphonates or calcitonin could explain the decrease in bone fragility that is disproportional to the gain in bone mineral density induced by these agents (Papapoulos, S. 1996. Bisphosphonates. Pharmacology and use in the treatment of osteoporosis. In Osteoporosis. R. Marcus, D. Feldman, and J. Kelsey, elditors. Academic Press, San Diego, Calif. 1209–1234; Cummings, et al., 1996. J. Bone Miner. Res. 11 (suppl):S102(Abstr.); Glorieux, et al., 1998. N. Engl. J. Med. 339:947–952). Indeed, osteocytes, the most abundant cell type in bone, are regularly spaced throughout the mineralized matrix and communicate with each other and with cells on the bone surface via cellular processes that run along the canaliculi; osteoblasts in turn communicate with cells of the bone marrow stroma which extend cellular projections onto endothelial cells inside the sinusoids (Marotti, et al., 1990. Ital. J. Min. Electrol. Metab. 4:93–106). Thus, a syncytium extends from the entombed osteocytes all the way to the vessel wall (Marotti, G. 1996. Ital. J. Anat. Embryol. 101:25–79; FIG. 12). As a consequence, the strategic location of osteocytes makes them excellent candidates for mechanosensory cells able to detect the need for bone augmentation or reduction during functional adaptation of the skeleton, and the need for repair of microdamage, and in both cases to transmit signals leading to the appropriate response (Aarden et al., 1994. J. Cell Biochem. 55:287–299). Osteocytes evidently sense changes in interstitial fluid flow through canaliculi produced by mechanical forces (Aarden et al., 1994. J. Cell Biochem. 55:287–299), and detect changes in the levels of hormones such as estrogen and glucocorticoids that influence their survival and which circulate in the same fluid (Noble, et al., 1997. Bone 20:273–282; Weinstein et al., 1998. J. Clin. Invest. 102:274–282). Disruption of the osteocyte network is likely to increase bone fragility and could account for the higher incidence of fractures in glucocorticoid-treated patients as compared to postmenopausal women, even though the BMD in the former is relatively higher (Peel, et al., 1995. Ann. Rheum. Dis. 54:801–806; Dennison, E. 1999. Epidemiology of glucocorticoid-induced osteoporosis. Osteoporosis Int. 9:S16(Abstr.)). Conversely, preservation of the osteocyte network could be one mechanism by which bisphosphonates or calcitonin decrease bone fragility.

The fate of the majority of osteoblasts that have completed their matrix synthesizing function is apoptosis, the other two fates being to become lining cells or osteocytes (Jilka, et al., 1998. J. Bone Miner. Res. 13:793–802). The frequency of osteoblast apoptosis in vivo seems to be such that changes in its timing and extent could have a significant impact in the number of osteoblasts present at the site of bone formation (Weinstein et al., 1998. J. Clin. Invest. 102:274–282; Jilka, et al., 1998. J. Bone Miner. Res. 13:793–802). Indeed, it has been recently shown that increased osteoblast apoptosis is at least partially responsible for the reduced bone formation in the osteopenia induced by glucocorticoid excess (Weinstein et al., 1998. J. Clin. Invest. 102:274–282; Weinstein, et al., 1998. Bone 23(suppl):S461(Abstr.)). Conversely, inhibition of osteoblast apoptosis is the most likely mechanism of the anabolic effect of intermittent administration of PTH (Jilka, et al., 1999. J. Clin. Invest. 104:439–446). In this report, bisphosphonates increase the survival of osteoblastic cells. Although similar anti-apoptotic effects of PTH and bisphosphonates in vitro, the in vivo effects of bisphosphonates on bone formation are not as readily demonstrated as those of intermittent PTH administration, probably because the slowing of remodeling by the former agents reduces the extent of osteoblast covered surface. But where osteoblasts are present, more bone is made, indicated by an increase in wall thickness (Chavassieux, et al., 1997. J. Clin. Invest. 100:1475–1480; Balena, et al., 1993. J. Clin. Invest. 92:2577–2586; Storm, et al., 1993. J. Bone Miner. Res. 8:199–208; Boyce, et al., 1995. J. Bone Miner. Res. 10:211–221).

The results reported herein could also be of importance to the recognized actions of bisphosphonates on the origination and/or progression of the basic multicellular unit (BMU). It has been proposed that targeting of osteoclast precursors to a specific location on bone depends on a "homing" signal given by lining cells; and that lining cells are instructed to do so by osteocytes—the only bone cells that can sense the need for remodeling at a specific time and place (Parfitt, et al., 1996. *J. Bone Miner. Res* 11:150–159). This, and the evidence that bisphosphonates affect osteoclasts not only directly but also indirectly via effects on osteoblastic cells (Nishikawa, et al., 1996. *Bone* 18:9–14; Sahni, et al., 1993. *J. Clin. Invest.* 91:2004–201 1; Vitte, et al., 1996. *Endocrinology* 137:2324–2333), raises the possibility that prolongation of the life span of osteocytes (and osteoblastic cells in general) may contribute to the reduction in the frequency of origination and/or premature termination of BMU progression that characterize the decrease in bone resorption induced by bisphosphonates (Papapoulos, S. 1996. Bisphosphonates. Pharmacology and use in the treatment of osteoporosis. In Osteoporosis. R. Marcus, D. Feldman, and J. Kelsey, editors. Academic Press, San Diego, Calif. 1209–1234; Parfitt, et al., 1996. *J. Bone Miner. Res* 11:150–159).

In conclusion, the studies reported herein raise for the first time the possibility that increased survival of osteoblasts and osteocytes may both contribute to the efficacy of bisphosphonates and calcitonin in the management of disease states due to loss of bone, such as glucocorticoid-induced osteoporosis. An increase in osteoblast work time may lead to a gradual increase in trabecular thickness while preservation of osteocytes may contribute to the anti-fracture efficacy of these agents, which is disproportional to the relatively modest increase in BMD.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for a compound that increases bone strength, that includes the steps of:

i. a) contacting osteocytes with a test compound; and b) comparing the number of apoptotic osteocytes contacted with the test compound with the number of apoptotic osteocytes in a control wherein osteocytes are not contacted with the compound;

ii. a) contacting osteoblasts with the test compound; and b) comparing the number of apoptotic osteoblasts contacted with the test compound with the number of apoptotic osteoblasts in a control wherein osteoblasts are not contacted with the test compound;

iii. a) contacting osteoclasts with the test compound; and b) comparing the number of apoptotic osteoclasts contacted with the test compound with the number of apoptotic osteoclasts in a control wherein osteoclasts are not contacted with the test compound; and iv. selecting a test compound that inhibits the apoptosis of osteocytes and osteoblasts and does not substantially affect the apoptosis of osteoclasts.

2. The method of claim 1, wherein said contacting occurs in vitro.

3. The method of claim 2, wherein said osteocytes are selected from the group consisting of MLO-Y4 cells and MLO-Y4 cells stably transfected with nuclear green fluorescent protein.

4. The method of claim 1, wherein said contacting occurs in vivo.

5. The method of claim 1, wherein said test compound is a bisphoshonate.

6. The method of claim 5, wherein said bisphosphonate is an amino-bisphosphonate.

7. The method of claim 1, wherein apoptosis of osteocytes is determined by a technique selected from the group consisting of fluorescent microscopy of MLO-Y4 cells stably transfected with nuclear green fluorescent protein, microscopy of stained cells, TUNEL analysis, Hoescht 33258 dye analysis, and video image analysis.

* * * * *

UNITED STATES PATENT AND TRADEMARK OFFICE
CERTIFICATE OF CORRECTION

PATENT NO. : 6,416,737 B1
DATED : July 9, 2002
INVENTOR(S) : Stavros C. Manolagas and Teresita Bellido It is certified that error appears in the above-identified patent and that said Letters Patent is hereby corrected as shown below:

<u>Title page,</u>
Item [73], Assignee, after "Board of Trustees of the University of Arkansas, Little Rock, AK (US)", add -- ; and Gador S.A., Buenos Aires (Argentina) --

Signed and Sealed this

Seventeenth Day of August, 2004

JON W. DUDAS
*Acting Director of the United States Patent and Trademark Office*